(12) United States Patent
Furuya et al.

(10) Patent No.: US 10,676,437 B2
(45) Date of Patent: Jun. 9, 2020

(54) FLUORINATED 4-(SUBSTITUTED AMINO)PHENYL CARBAMATE DERIVATIVES

(71) Applicant: SciFluor Life Sciences, Inc., Cambridge, MA (US)

(72) Inventors: Takeru Furuya, Cambridge, MA (US); Ben C. Askew, Marshfield, MA (US); D. Scott Edwards, Bedford, MA (US)

(73) Assignee: SciFluor Life Sciences, Inc., Boston, MA (US)

( * ) Notice: Subject to any disclaimer, the term of this patent is extended or adjusted under 35 U.S.C. 154(b) by 0 days.

(21) Appl. No.: 16/218,759

(22) Filed: Dec. 13, 2018

(65) Prior Publication Data

US 2019/0177274 A1 Jun. 13, 2019

Related U.S. Application Data

(60) Provisional application No. 62/597,979, filed on Dec. 13, 2017.

(51) Int. Cl.
| | |
|---|---|
| *C07D 211/44* | (2006.01) |
| *C07C 233/07* | (2006.01) |
| *C07D 217/02* | (2006.01) |
| *A61P 25/08* | (2006.01) |
| *C07C 233/43* | (2006.01) |

(52) U.S. Cl.
CPC ............ *C07D 211/44* (2013.01); *A61P 25/08* (2018.01); *C07C 233/07* (2013.01); *C07C 233/43* (2013.01); *C07D 217/02* (2013.01)

(58) Field of Classification Search
CPC ............................... C07D 211/44; A61P 25/08
See application file for complete search history.

(56) References Cited

U.S. PATENT DOCUMENTS

| | | |
|---|---|---|
| 5,384,330 A | 1/1995 | Dieter et al. |
| 8,916,133 B2 | 12/2014 | Duggan et al. |
| 9,556,114 B2 * | 1/2017 | Duggan ................ C07C 271/28 |
| 2013/0287686 A1 | 10/2013 | Duggan et al. |
| 2017/0355679 A1 | 12/2017 | Edwards et al. |

FOREIGN PATENT DOCUMENTS

| | | |
|---|---|---|
| WO | WO 01/01970 A2 | 1/2001 |
| WO | WO 2006/029623 A1 | 3/2006 |
| WO | WO 2008/024398 A2 | 2/2008 |
| WO | WO 2014/048165 A1 | 4/2014 |
| WO | WO 2017/214539 A1 | 12/2017 |

* cited by examiner

*Primary Examiner* — Golam M Shameem
(74) *Attorney, Agent, or Firm* — Cooley LLP; Heidi A. Erlacher; Chen Chen

(57) ABSTRACT

The application relates to 4-(substituted amino)phenyl carbamate derivatives, or pharmaceutically acceptable salts or solvates thereof, as KCNQ2/3 potassium channel modulators, and methods of their uses.

17 Claims, No Drawings

FLUORINATED 4-(SUBSTITUTED AMINO)PHENYL CARBAMATE DERIVATIVES

RELATED APPLICATION

This application claims priority to and the benefit of U.S. Provisional Application No. 62/597,979, filed on Dec. 13, 2017, the entire contents of which are incorporated herein by reference.

BACKGROUND

Epilepsy is one of the most common chronic neurological disorders, and affects approximately 50 million people worldwide. Epilepsy patients have significantly increased morbidity, including closed head injury, fractures, burns, dental injury and soft tissue injury. Decline in or worsening of memory, cognition, depression and sexual function and other lifestyle limitations occur frequently in epilepsy patients. Epilepsy patients also have an increased risk of mortality compared to the general population.

Although various pharmacologic agents are approved to treat epilepsy, many patients are not adequately treated with the currently available options. It is estimated that nearly a third of patients with epilepsy have either intractable or uncontrolled seizures or significant adverse side effects.

Ezogabine or retigabine, also known as ethyl N-[2-amino-4-[(4-fluorophenyl) methylamino]phenyl]carbamate, is an anticonvulsant used as a treatment for partial epilepsies. Ezogabine works primarily as a potassium channel opener, i.e., by activating KCNQ2/3 voltage-gated potassium channels in the brain. Ezogabine was approved by the FDA and is marketed as Potiga™ and Trobalt™. U.S. Pat. No. 5,384,330 and WO 01/01970 describe ezogabine and its use. The most common adverse events with ezogabine are central nervous system effects, particularly dizziness and somnolence. Occasional instances of urinary difficulty may require surveillance. Recently, ezogabine has been associated with skin discoloration and eye pigmentation changes in patients. These more serious side-effects have resulted in the marketing application holders and its removal from the market in 2017.

Because of the beneficial activities seen with ezogabine, there is a continuing interest in developing new compounds to treat epilepsy and other conditions ameliorated by KCNQ2/3 potassium channel opening.

SUMMARY OF THE APPLICATION

The present application relates to a compound of formula A:

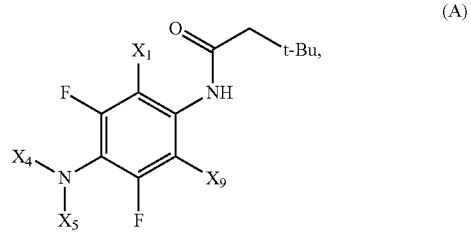

(A)

or a pharmaceutically acceptable salt or solvate thereof, wherein the compound of formula A is disclosed in detail herein below.

The application also relates to a pharmaceutical composition comprising a compound of the present application, or a pharmaceutically acceptable salt or solvate thereof, and a pharmaceutically acceptable carrier.

The application also relates to a method of modulating a KCNQ2/3 potassium channel, comprising administering to a subject in need thereof, a therapeutically effective amount of a compound of the present application, or a pharmaceutically acceptable salt or solvate thereof.

The application also relates to a compound of the present application, or a pharmaceutically acceptable salt or solvate thereof, for use in modulating a KCNQ2/3 potassium channel.

The application also relates to a compound of the present application, or a pharmaceutically acceptable salt or solvate thereof, for use in the manufacture of a medicament for modulating a KCNQ2/3 potassium channel.

The present application also relates to use of a compound of the present application, or a pharmaceutically acceptable salt or solvate thereof, in the manufacture of a medicament for modulation of a KCNQ2/3 potassium channel.

The application further relates to a method of treating or preventing a disease or disorder which can be ameliorated by KCNQ2/3 potassium channel opening, comprising administering to a subject in need thereof, a therapeutically effective amount of a compound of the present application, or a pharmaceutically acceptable salt or solvate thereof.

The application also relates to a compound of the present application, or a pharmaceutically acceptable salt or solvate thereof, for use in treating or preventing a disease or disorder which can be ameliorated by KCNQ2/3 potassium channel opening.

The application also relates to a compound of the present application, or a pharmaceutically acceptable salt or solvate thereof, for use in the manufacture of a medicament for treating or preventing a disease or disorder which can be ameliorated by KCNQ2/3 potassium channel opening.

The present application also relates to use of a compound of the present application, or a pharmaceutically acceptable salt or solvate thereof, in the manufacture of a medicament for the treatment or prevention of a disease or disorder which can be ameliorated by KCNQ2/3 potassium channel opening.

The application further relates to a method of treating or preventing epilepsy, comprising administering to a subject in need thereof, a therapeutically effective amount of a compound of the present application, or a pharmaceutically acceptable salt or solvate thereof.

The application also relates to a compound of the present application, or a pharmaceutically acceptable salt or solvate thereof, for use in treating or preventing epilepsy.

The application also relates to a compound of the present application, or a pharmaceutically acceptable salt or solvate thereof, for use in the manufacture of a medicament for treating or preventing epilepsy.

The present application also relates to the use of a compound of the present application, or a pharmaceutically acceptable salt or solvate thereof, in the manufacture of a medicament for the treatment or prevention of epilepsy.

Unless otherwise defined, all technical and scientific terms used herein have the same meaning as commonly understood by one of ordinary skill in the art to which this application belongs. In the case of conflict, the present specification, including definitions, will control. In the specification, the singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the present application. In addition, the materials, methods, and examples are illustrative only and are not intended to be limiting.

Other features and advantages of the application will be apparent from the following detailed description and claims.

DETAILED DESCRIPTION OF THE APPLICATION

For purposes of the present application, the following definitions will be used (unless expressly stated otherwise):

The term "a compound of the application" or "compounds of the application" refers to any compound disclosed herein, e.g., a compound of any of the formulae described herein, including formula A, Ia, Ib, IIa, IIb, IIIa, IIIb, IVa, or IVb, and/or an individual compound explicitly disclosed herein. Whenever the term is used in the context of the present application it is to be understood that the reference is being made to the free base, a deuterium labeled compound, and the corresponding pharmaceutically acceptable salts or solvates thereof, provided that such is possible and/or appropriate under the circumstances.

The term "pharmaceutical" or "pharmaceutically acceptable" when used herein as an adjective, means substantially non-toxic and substantially non-deleterious to the recipient.

By "pharmaceutical formulation" it is further meant that the carrier, solvent, excipient, and salt must be compatible with the active ingredient of the formulation (e.g., a compound of the application). It is understood by those of ordinary skill in this art that the terms "pharmaceutical formulation" and "pharmaceutical composition" are generally interchangeable, and they are so used for the purposes of this application.

Some of the compounds of the present application may exist in unsolvated as well as solvated forms such as, for example, hydrates.

"Solvate" means a solvent addition form that contains either a stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. In the hydrates, the water molecules are attached through secondary valencies by intermolecular forces, in particular hydrogen bridges. Solid hydrates contain water as so-called crystal water in stoichiometric ratios, where the water molecules do not have to be equivalent with respect to their binding state. Examples of hydrates are sesquihydrates, monohydrates, dihydrates or trihydrates. Equally suitable are the hydrates of salts of the compounds of the application.

Physiologically acceptable, i.e., pharmaceutically compatible or pharmaceutically acceptable, salts can be salts of the compounds of the application with inorganic or organic acids. Preference is given to salts with inorganic acids, such as, for example, hydrochloric acid, hydrobromic acid, phosphoric acid or sulphuric acid, or to salts with organic carboxylic or sulphonic acids, such as, for example, acetic acid, trifluoroacetic acid, propionic acid, maleic acid, fumaric acid, malic acid, citric acid, tartaric acid, lactic acid, benzoic acid, or methanesulphonic acid, ethanesulphonic acid, benzenesulphonic acid, toluenesulphonic acid or naphthalenedisulphonic acid. Other pharmaceutically compatible salts which may be mentioned are salts with customary bases, such as, for example, alkali metal salts (for example sodium or potassium salts), alkaline earth metal salts (for example calcium or magnesium salts) or ammonium salts, derived from ammonia or organic amines, such as, for example, diethylamine, triethylamine, ethyldiisopropylamine, procaine, dibenzylamine, N-methylmorpholine, dihydroabietylamine or methylpiperidine. Representative salts include the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamottle (embonate), palmitate, pantothenate, phosphate/diphosphate, polygalacturonate, salicylate, stearate, sulfate, subacetate, succinate, tannate, tartrate, teoclate, tosylate, triethiodide, and valerate.

The compounds of the application may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers. It is intended that all of the possible optical isomers and diastereomers in mixtures and as pure or partially purified compounds are included within the ambit of the application. The application is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

In the present specification, the structural formula of the compound represents a certain isomer for convenience in some cases, but the present application includes all isomers, such as geometrical isomers, optical isomers based on an asymmetrical carbon, stereoisomers, tautomers, and the like.

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., *Angew. Chem. Inter. Edit.* 1966, 5, 385; errata 511; Cahn et al., *Angew. Chem.* 1966, 78, 413; Cahn and Ingold, *J. Chem. Soc.* 1951 (London), 612; Cahn et al., *Experientia* 1956, 12, 81; Cahn, *J. Chem. Educ.* 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine. In one example,

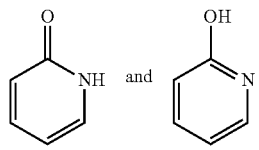

are tautomers to each other.

It is to be understood that the compounds of the present application may be depicted as different tautomers. It should also be understood that when compounds have tautomeric forms, all tautomeric forms are intended to be included in the scope of the present application, and the naming of the compounds does not exclude any tautomer form.

If desired, racemic mixtures of the compounds may be separated so that the individual enantiomers are isolated. The separation can be carried out by methods well known in the art, such as contacting a racemic mixture of compounds with an enantiomerically pure compound to form a diastereomeric mixture, followed by separation of the individual diastereomers by standard methods, such as fractional crystallization or chromatography. The diastereomeric mixture is often a mixture of diasteriomeric salts formed by contacting a racemic mixture of compounds with an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which are well known in the art.

The application also includes one or more metabolites of a compound of the application.

The present application also comprehends deuterium labeled compounds of each of the formulae described herein or the individual compounds specifically disclosed, wherein a hydrogen atom is replaced by a deuterium atom. The deuterium labeled compounds comprise a deuterium atom having an abundance of deuterium that is substantially greater than the natural abundance of deuterium, e.g., 0.015%.

The term "deuterium enrichment factor" as used herein means the ratio between the deuterium abundance and the natural abundance of a deuterium. In one aspect, a compound of the application has a deuterium enrichment factor for each deuterium atom of at least 3500 (52.5% deuterium incorporation at each deuterium atom), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Deuterium labeled compounds can be prepared using any of a variety of art-recognized techniques. For example, deuterium labeled compounds of each of the formulae described herein or the compounds listed in Table 1 can generally be prepared by carrying out the procedures described herein, by substituting a readily available deuterium labeled reagent for a non-deuterium labeled reagent.

A compound of the application or a pharmaceutically acceptable salt or solvate thereof that contains the aforementioned deuterium atom(s) is within the scope of the application. Further, substitution with deuterium, i.e., $^2$H, can afford certain therapeutic advantages resulting from greater metabolic stability, for example, increased in vivo half-life and/or reduced dosage requirements.

As used herein, the term "treat", "treating", or "treatment" herein, is meant decreasing the symptoms, markers, and/or any negative effects of a disease, disorder or condition in any appreciable degree in a patient who currently has the condition. The term "treat", "treating", or "treatment" includes alleviating symptoms of a disease, disorder, or condition, e.g., alleviating the symptoms of epilepsy. In some embodiments, treatment may be administered to a subject who exhibits only early signs of the condition for the purpose of decreasing the risk of developing the disease, disorder, and/or condition.

As used herein, the term "prevent", "prevention", or "preventing" refers to any method to partially or completely prevent or delay the onset of one or more symptoms or features of a disease, disorder, and/or condition. Prevention may be administered to a subject who does not exhibit signs of a disease, disorder, and/or condition.

As used herein, "subject" means a human or animal (in the case of an animal, more typically a mammal). In one embodiment, the subject is a human. In one embodiment, the subject is a male. In one embodiment, the subject is a female.

As used herein, the term a "fluorinated derivative" is a derivative compound that has the same chemical structure as the original compound, except that at least one atom is replaced with a fluorine atom or with a group of atoms containing at least one fluorine atom.

The problem to be solved by the present application is the identification of novel compounds for the treatment and/or prevention of epilepsy and/or other diseases or disorders ameliorated by KCNQ2/3 potassium channel opening. Although drugs for epilepsy and related disorders are available, these drugs are often not suitable for many patients for a variety of reasons. Many epilepsy drugs are associated with adverse effects. For example, many of the available epilepsy drugs are believed to significantly increase the risk of birth defects if taken during the first trimester of pregnancy. Other adverse side effects include urinary retention, neuro-psychiatric symptoms including hallucinations and psychosis, dizziness and somnolence, QT-prolonging effect, and increased risk of suicidal behavior and ideation. Some epilepsy drugs require administration of high doses due to extensive metabolism into inactive or less potent metabolites. The present application provides the solution of new fluorinated 4-(substituted amino)phenylcarbamate compounds for treating epilepsy and other diseases or disorders ameliorated by KCNQ2/3 potassium channel opening. The compounds described herein have the advantage of providing improved potency, selectivity, tissue penetration, half-life, and/or metabolic stability.

Compounds of the Application

The present application relates to a compound of formula A:

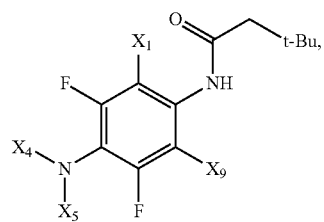

(A)

or a pharmaceutically acceptable salt or solvate thereof, wherein:

$X_1$ and $X_9$ are each independently methyl or ethyl;

$X_4$ is H, $C_1$-$C_4$ alkyl, $C_2$-$C_6$ alkenyl, or $C_2$-$C_6$ alkynyl;

$X_5$ is phenyl-$(CX_8X_8)_m$, wherein the phenyl is optionally substituted with one or more substituents independently selected from deuterium, F, $SF_5$, $C_1$-$C_4$ alkyl, $C_1$-$C_4$ alkyl substituted with one or more F, $C_1$-$C_4$ alkoxy, and $C_1$-$C_4$ alkoxy substituted with one or more F; or $X_4$ and $X_5$, together with the nitrogen atom to which they are attached, form a 5- to 7-membered heterocyclic ring comprising 1 or 2 heteroatoms selected from N, O, and S, wherein the heterocyclic ring is optionally substituted with one or more substituents independently selected from deuterium, F, $SF_5$, $C_1$-$C_4$ alkyl, $C_1$-$C_4$ alkyl substituted with one or more F, $C_1$-$C_4$ alkoxy, and $C_1$-$C_4$ alkoxy substituted with one or more F, or two substituents attached to adjacent carbon atoms on the heterocyclic ring, together with the carbon atoms to which they are attached, form a phenyl optionally substituted with one or more substituents independently selected from deuterium, F, $SF_5$, $C_1$-$C_4$ alkyl, $C_1$-$C_4$ alkyl substituted with one or more F, $C_1$-$C_4$ alkoxy, and $C_1$-$C_4$ alkoxy substituted with one or more F;

each $X_5$ is independently H, deuterium, F, $C_1$-$C_4$ alkyl, or $C_1$-$C_4$ alkyl substituted with one or more F; and m is 1, 2, or 3.

In one embodiment, the compound of formula A is of formula Ia:

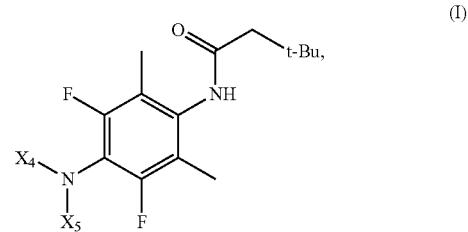

(I)

or a pharmaceutically acceptable salt or solvate thereof, wherein $X_4$, $X_5$, $X_8$, and m are each as defined above in formula A.

In one embodiment, the compound of formula A is of formula Ib:

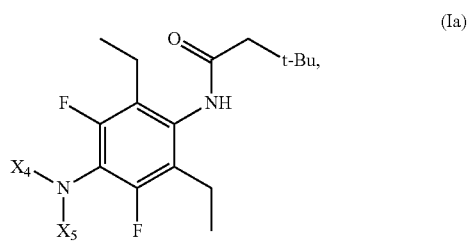

(Ia)

or a pharmaceutically acceptable salt or solvate thereof, wherein $X_4$, $X_5$, $X_8$, and m are each as defined above in formula A.

For a compound of formula A, Ia, or Ib, $X_1$, $X_4$, $X_5$, $X_8$, $X_9$, and m can each be, where applicable, selected from the groups described herein below, and any group described herein for any of $X_1$, $X_4$, $X_5$, $X_8$, $X_9$, and m can be combined, where applicable, with any group described herein for one or more of the remainder of $X_1$, $X_4$, $X_5$, $X_8$, $X_9$, and m.

In one embodiment, $X_1$ and $X_9$ are each methyl.

In one embodiment, $X_1$ and $X_9$ are each ethyl.

In one embodiment, one of $X_1$ and $X_9$ is methyl and the other is ethyl.

In one embodiment, $X_4$ is H.

In one embodiment, $X_4$ is $C_1$-$C_4$ alkyl, $C_2$-$C_6$ alkenyl, or $C_2$-$C_6$ alkynyl.

In one embodiment, $X_4$ is selected from methyl, ethyl, propyl, i-propyl, butyl, i-butyl, and t-butyl.

In one embodiment, $X_4$ is selected from ethenyl, propenyl (e.g., 1-propenyl or 2-propenyl), butenyl (e.g., 1-butenyl, 2-butenyl, or 3-butenyl), pentenyl (e.g., 1-pentenyl, 2-pentenyl, 3-pentenyl, or 4-pentenyl), and hexenyl (e.g., 1-hexenyl, 2-hexenyl, 3-hexenyl, 4-hexenyl, or 5-hexenyl). In one embodiment, $X_4$ is 1-propenyl or 2-propenyl.

In one embodiment, $X_4$ is selected from ethynyl, propynyl (e.g., 1-propynyl or 2-propynyl), butynyl (e.g., 1-butynyl, 2-butynyl, or 3-butynyl), pentynyl (e.g., 1-pentynyl, 2-pentynyl, 3-pentynyl, or 4-pentynyl), and hexynyl (e.g., 1-hexynyl, 2-hexynyl, 3-hexynyl, 4-hexynyl, or 5-hexynyl). In one embodiment, $X_4$ is 1-propynyl or 2-propynyl.

In one embodiment, $X_5$ is phenyl-$(CX_8X_8)$, phenyl-$(CX_8X_8)_2$, or phenyl-$(CX_8X_8)_3$, wherein the phenyl is optionally substituted with one or more substituents independently selected from deuterium, F, $SF_5$, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F).

In one embodiment, the phenyl is substituted with one or more substituents independently selected from F, $C_1$-$C_4$ alkyl substituted with one or more F (e.g., methyl, ethyl, propyl, i-propyl, butyl, i-butyl, or t-butyl, each of which is substituted with one or more F), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $SF_5$, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, the phenyl is substituted with one or more substituents independently selected from F, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, the phenyl is substituted with one or more groups independently selected from F, $CF_3$, $CHF_2$, $CH_2F$, $OCF_3$, $OCHF_2$, and $OCH_2F$. In one embodiment, the phenyl is substituted with one or more substituents independently selected from F, $CF_3$, and $OCF_3$.

In one embodiment, the phenyl is substituted with one or more substituents independently selected from F and $C_1$-$C_4$ alkyl substituted with one or more F (e.g., methyl, ethyl, propyl, i-propyl, butyl, i-butyl, or t-butyl, each of which is substituted with one or more F). In one embodiment, the phenyl is substituted with one or more substituents independently selected from F, $SF_5$, $CF_3$, $CHF_2$, $CH_2F$, $CH_2CF_3$, $CH_2CHF_2$, and $CH_2CH_2F$. In one embodiment, the phenyl is substituted with one or more substituents independently selected from F, $CF_3$, $CHF_2$, $CH_2F$, $CH_2CF_3$, $CH_2CHF_2$, and $CH_2CH_2F$. In one embodiment, the phenyl is substituted with one or more groups independently selected from F, $CF_3$, $CHF_2$, and $CH_2F$. In one embodiment, the phenyl is substituted with one or more substituents independently selected from F and $CF_3$.

In one embodiment, the phenyl is substituted with one or more substituents independently selected from F and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $SF_5$, $OCF_3$, $OCHF_2$, $OCH_2F$, $OCH_2CF_3$, $OCH_2CHF_2$, and $OCH_2CH_2F$. In one embodiment, the phenyl is substituted with one or more substituents independently selected from F, $OCF_3$, $OCHF_2$, $OCH_2F$, $OCH_2CF_3$, $OCH_2CHF_2$, and $OCH_2CH_2F$. In one embodiment, the phenyl is substituted with one or more groups independently selected from F, $CF_3$, $CHF_2$, $CH_2F$, $OCF_3$, $OCHF_2$, and $OCH_2F$. In one embodiment, the phenyl is substituted with one or more substituents independently selected from F and $OCF_3$.

In one embodiment, the phenyl is substituted with one or more substituents independently selected from $C_1$-$C_4$ alkyl (e.g., methyl, ethyl, propyl, i-propyl, butyl, i-butyl, or t-butyl) and $C_1$-$C_4$ alkoxy (e.g., methoxy, ethoxy, propoxy, i-propoxy, butoxy, i-butoxy, or t-butoxy). In one embodiment, the phenyl is substituted with one or more substituents independently selected from $CH_3$, $CH_2CH_3$, $OCH_3$, and $OCH_2CH_3$. In one embodiment, the phenyl is substituted with one or more substituents independently selected from $CH_3$ and $CH_2CH_3$. In one embodiment, the phenyl is substituted with one or more $CH_3$. In one embodiment, the phenyl is substituted with one or more substituents independently selected from $OCH_3$ and $OCH_2CH_3$. In one embodiment, the phenyl is substituted with one or more $OCH_3$.

In one embodiment, the substituent is attached at the para-position on the phenyl ring. In one embodiment, the substituent(s) are attached at the meta-position(s) on the phenyl ring. In one embodiment, the substituent(s) are attached at the ortho-position(s) on the phenyl ring.

In one embodiment, $X_5$ is 2-fluoro-benzyl. In one embodiment, $X_5$ is 3-fluoro-benzyl. In one embodiment, $X_5$ is 4-fluoro-benzyl. In one embodiment, $X_5$ is 2-fluoro-benzyl. In one embodiment, $X_5$ is 3-fluoro-benzyl. In one embodiment, $X_5$ is 2-trifluoromethyl-benzyl. In one embodiment, $X_5$ is 3-trifluoromethyl-benzyl. In one embodiment, $X_5$ is 4-trifluoromethyl-benzyl. In one embodiment, $X_5$ is 2-trifluoromethoxy-benzyl. In one embodiment, $X_5$ is 3-trifluoromethoxy-benzyl. In one embodiment, $X_5$ is 4-trifluoromethoxy-benzyl.

In one embodiment, each $X_8$ is H. In one embodiment, at least one $X_8$ is deuterium, F, $C_1$-$C_4$ alkyl (e.g., methyl, ethyl, propyl, i-propyl, butyl, i-butyl, or t-butyl), or $C_1$-$C_4$ alkyl substituted with one or more F (e.g., methyl, ethyl, propyl, i-propyl, butyl, i-butyl, or t-butyl, each of which is substituted with one or more F). In one embodiment, at least one $X_8$ is deuterium. In one embodiment, at least one $X_8$ is F, $C_1$-$C_4$ alkyl (e.g., methyl, ethyl, propyl, i-propyl, butyl, i-butyl, or t-butyl), or $C_1$-$C_4$ alkyl substituted with one or more F (e.g., methyl, ethyl, propyl, i-propyl, butyl, i-butyl, or t-butyl, each of which is substituted with one or more F).

In one embodiment, at least one $X_8$ is $C_1$-$C_4$ alkyl (e.g., methyl, ethyl, propyl, i-propyl, butyl, i-butyl, or t-butyl) or $C_1$-$C_4$ alkyl substituted with one or more F (e.g., methyl, ethyl, propyl, i-propyl, butyl, i-butyl, or t-butyl, each of which is substituted with one or more F). In one embodiment, at least one $X_8$ is F or $C_1$-$C_4$ alkyl substituted with one or more F (e.g., methyl, ethyl, propyl, i-propyl, butyl, i-butyl, or t-butyl, each of which is substituted with one or more F). In one embodiment, at least one $X_8$ is $C_1$-$C_4$ alkyl (e.g., methyl, ethyl, propyl, i-propyl, butyl, i-butyl, or t-butyl). In one embodiment, at least one $X_8$ is $C_1$-$C_4$ alkyl substituted with one or more F (e.g., methyl, ethyl, propyl, i-propyl, butyl, i-butyl, or t-butyl, each of which is substituted with one or more F). In one embodiment, at least one $X_8$ is F.

In one embodiment, $X_4$ and $X_8$, together with the nitrogen atom to which they are attached, form a 5- to 7-membered heterocyclic ring comprising 1 or 2 heteroatoms selected from N, O, and S (e.g., pyrrolidinyl, tetrahydrofuranyl, tetrahydrothiophenyl, oxazolidinyl, isoxazolidinyl, thiazolidinyl, isothiazolidinyl, piperidinyl, piperazinyl, tetrahydropyranyl, tetrahydrothiapyranyl, dioxanyl, morpholinyl, oxazinanyl, thiazinanyl, or oxathianyl). In one embodiment, $X_4$ and $X_5$, together with the nitrogen atom to which they are attached, form a 5- to 7-membered heterocyclic ring comprising 1 heteroatom selected from N, O, and S. In one embodiment, $X_4$ and $X_5$, together with the nitrogen atom to which they are attached, form a 5- or 6-membered heterocyclic ring comprising 1 heteroatom selected from N, O, and S. In one embodiment, $X_4$ and $X_5$, together with the nitrogen atom to which they are attached, form a 5- or 6-membered heterocyclic ring comprising 1 heteroatom selected from N and O. In one embodiment, $X_4$ and $X_5$, together with the nitrogen atom to which they are attached, form a pyrrolidinyl or piperidinyl ring.

In one embodiment, $X_4$ and $X_5$, together with the nitrogen atom to which they are attached, form a 5- to 7-membered heterocyclic ring optionally substituted with one or more substituents independently selected from deuterium, F, $SF_5$, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the heterocyclic ring is substituted with one or more substituents independently selected from F, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the heterocyclic ring is substituted with one or more substituents independently selected from $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the heterocyclic ring is substituted with one or more substituents independently selected from F, $C_1$-$C_4$ alkyl substituted with one or more F (e.g., methyl, ethyl, propyl, i-propyl, butyl, i-butyl, or t-butyl, each of which is substituted with one or more F), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the heterocyclic ring is substituted with one or more substituents independently selected from F, $SF_5$, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, the heterocyclic ring is substituted with one or more substituents independently selected from F, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, the heterocyclic ring is substituted with one or more groups independently selected from F, $CF_3$, $CHF_2$, $CH_2F$, $OCF_3$, $OCHF_2$, and $OCH_2F$. In one embodiment, the heterocyclic ring is substituted with one or more substituents independently selected from F, $CF_3$, and $OCF_3$. In one embodiment, the heterocyclic ring is substituted with one or more substituents independently selected from F and $C_1$-$C_4$ alkyl substituted with one or more F (e.g., methyl, ethyl, propyl, i-propyl, butyl, i-butyl, or t-butyl, each of which is substituted with one or more F). In one embodiment, the heterocyclic ring is substituted with one or more substituents independently selected from F, $SF_5$, $CF_3$, $CHF_2$, $CH_2F$, $CH_2CF_3$, $CH_2CHF_2$, and $CH_2CH_2F$. In one embodiment, the heterocyclic ring is substituted with one or more substituents independently selected from F, $CF_3$, $CHF_2$, $CH_2F$, $CH_2CF_3$, $CH_2CHF_2$, and $CH_2CH_2F$. In one embodiment, the heterocyclic ring is substituted with one or more groups independently selected from F, $CF_3$, $CHF_2$, and $CH_2F$. In one embodiment, the heterocyclic ring is substituted with one or more substituents independently selected from F and $CF_3$. In one embodiment, the heterocyclic ring is substituted with one or more substituents independently selected from F and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the heterocyclic ring is substituted with one or more substituents independently selected from F, $SF_5$, $OCF_3$, $OCHF_2$, $OCH_2F$, $OCH_2CF_3$, $OCH_2CHF_2$, and $OCH_2CH_2F$. In one embodiment, the heterocyclic ring is substituted with one or more substituents independently selected from F, $OCF_3$, $OCHF_2$, $OCH_2F$, $OCH_2CF_3$, $OCH_2CHF_2$, and $OCH_2CH_2F$. In one embodiment, the heterocyclic ring is substituted with one or more groups independently selected from F, $CF_3$, $CHF_2$, $CH_2F$, $OCF_3$, $OCHF_2$, and $OCH_2F$. In one embodiment, the heterocyclic ring is substituted with one or more substituents independently selected from F and $OCF_3$. In one embodiment, the heterocyclic ring is substituted with one or more substituents independently selected from $C_1$-$C_4$ alkyl (e.g., methyl, ethyl, propyl, i-propyl, butyl, i-butyl, or t-butyl) and $C_1$-$C_4$ alkoxy (e.g., methoxy, ethoxy, propoxy, i-propoxy, butoxy, i-butoxy, or t-butoxy). In one embodiment, the heterocyclic ring is substituted with one or more substituents independently selected from $CH_3$, $CH_2CH_3$, $OCH_3$, and $OCH_2CH_3$. In one embodiment, the heterocyclic ring is substituted with one or more substituents independently selected from $CH_3$ and $CH_2CH_3$. In one embodiment, the heterocyclic ring is substituted with one or more $CH_3$. In one embodiment, the heterocyclic ring is substituted with one or more substituents independently selected from $OCH_3$ and OCH$_2$CH$_3$. In one embodiment, the heterocyclic ring is substituted with one or more OCH$_3$.

In one embodiment, X$_4$ and X$_5$, together with the nitrogen atom to which they are attached, form a 5- to 7-membered heterocyclic ring substituted with two or more substituents, wherein two substituents attached to adjacent carbon atoms on the heterocyclic ring, together with the carbon atoms to which they are attached, form a phenyl optionally substituted with one or more substituents independently selected from deuterium, F, SF$_5$, C$_1$-C$_4$ alkyl (e.g., methyl, ethyl, propyl, i-propyl, butyl, i-butyl, or t-butyl), C$_1$-C$_4$ alkyl substituted with one or more F (e.g., methyl, ethyl, propyl, i-propyl, butyl, i-butyl, or t-butyl, each of which is substituted with one or more F), C$_1$-C$_4$ alkoxy (e.g., methoxy, ethoxy, propoxy, i-propoxy, butoxy, i-butoxy, or t-butoxy), and C$_1$-C$_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, C$_1$-C$_4$ alkyl (e.g., methyl, ethyl, propyl, i-propyl, butyl, i-butyl, or t-butyl), C$_1$-C$_4$ alkyl substituted with one or more F (e.g., methyl, ethyl, propyl, i-propyl, butyl, i-butyl, or t-butyl, each of which is substituted with one or more F), C$_1$-C$_4$ alkoxy (e.g., methoxy, ethoxy, propoxy, i-propoxy, butoxy, i-butoxy, or t-butoxy), and C$_1$-C$_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from C$_1$-C$_4$ alkyl (e.g., methyl, ethyl, propyl, i-propyl, butyl, i-butyl, or t-butyl), C$_1$-C$_4$ alkyl substituted with one or more F (e.g., methyl, ethyl, propyl, i-propyl, butyl, i-butyl, or t-butyl, each of which is substituted with one or more F), C$_1$-C$_4$ alkoxy (e.g., methoxy, ethoxy, propoxy, i-propoxy, butoxy, i-butoxy, or t-butoxy), and C$_1$-C$_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, C$_1$-C$_4$ alkyl substituted with one or more F (e.g., methyl, ethyl, propyl, i-propyl, butyl, i-butyl, or t-butyl, each of which is substituted with one or more F), and C$_1$-C$_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, SF$_5$, CF$_3$, CHF$_2$, CH$_2$F, CH$_2$CF$_3$, CH$_2$CHF$_2$, CH$_2$CH$_2$F, OCF$_3$, OCHF$_2$, OCH$_2$F, OCH$_2$CF$_3$, OCH$_2$CHF$_2$, and OCH$_2$CH$_2$F. In one embodiment, the phenyl is substituted with one or more substituents independently selected from F, CF$_3$, CHF$_2$, CH$_2$F, CH$_2$CF$_3$, CH$_2$CHF$_2$, CH$_2$CH$_2$F, OCF$_3$, OCHF$_2$, OCH$_2$F, OCH$_2$CF$_3$, OCH$_2$CHF$_2$, and OCH$_2$CH$_2$F. In one embodiment, the phenyl is substituted with one or more groups independently selected from F, CF$_3$, CHF$_2$, CH$_2$F, OCF$_3$, OCHF$_2$, and OCH$_2$F. In one embodiment, the phenyl is substituted with one or more substituents independently selected from F, CF$_3$, and OCF$_3$. In one embodiment, the phenyl is substituted with one or more substituents independently selected from F and C$_1$-C$_4$ alkyl substituted with one or more F (e.g., methyl, ethyl, propyl, i-propyl, butyl, i-butyl, or t-butyl, each of which is substituted with one or more F). In one embodiment, the phenyl is substituted with one or more substituents independently selected from F, SF$_5$, CF$_3$, CHF$_2$, CH$_2$F, CH$_2$CF$_3$, CH$_2$CHF$_2$, and CH$_2$CH$_2$F. In one embodiment, the phenyl is substituted with one or more substituents independently selected from F, CF$_3$, CHF$_2$, CH$_2$F, CH$_2$CF$_3$, CH$_2$CHF$_2$, and CH$_2$CH$_2$F. In one embodiment, the phenyl is substituted with one or more groups independently selected from F, CF$_3$, CHF$_2$, and CH$_2$F. In one embodiment, the phenyl is substituted with one or more substituents independently selected from F and CF$_3$. In one embodiment, the phenyl is substituted with one or more substituents independently selected from F and C$_1$-C$_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, SF$_5$, OCF$_3$, OCHF$_2$, OCH$_2$F, OCH$_2$CF$_3$, OCH$_2$CHF$_2$, and OCH$_2$CH$_2$F. In one embodiment, the phenyl is substituted with one or more substituents independently selected from F, OCF$_3$, OCHF$_2$, OCH$_2$F, OCH$_2$CF$_3$, OCH$_2$CHF$_2$, and OCH$_2$CH$_2$F. In one embodiment, the phenyl is substituted with one or more groups independently selected from F, CF$_3$, CHF$_2$, CH$_2$F, OCF$_3$, OCHF$_2$, and OCH$_2$F. In one embodiment, the phenyl is substituted with one or more substituents independently selected from F and OCF$_3$. In one embodiment, the phenyl is substituted with one or more substituents independently selected from C$_1$-C$_4$ alkyl (e.g., methyl, ethyl, propyl, i-propyl, butyl, i-butyl, or t-butyl) and C$_1$-C$_4$ alkoxy (e.g., methoxy, ethoxy, propoxy, i-propoxy, butoxy, i-butoxy, or t-butoxy). In one embodiment, the phenyl is substituted with one or more substituents independently selected from CH$_3$, CH$_2$CH$_3$, OCH$_3$, and OCH$_2$CH$_3$. In one embodiment, the phenyl is substituted with one or more substituents independently selected from CH$_3$ and CH$_2$CH$_3$. In one embodiment, the phenyl is substituted with one or more CH$_3$. In one embodiment, the phenyl is substituted with one or more substituents independently selected from OCH$_3$ and OCH$_2$CH$_3$. In one embodiment, the phenyl is substituted with one or more OCH$_3$.

In one embodiment, X$_4$ and X$_5$, together with the nitrogen atom to which they are attached, form a heterocyclic ring selected from

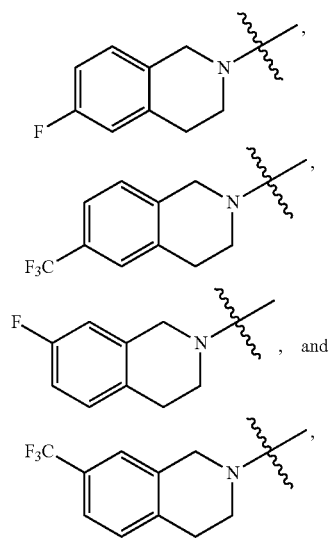

wherein the nitrogen atom is the nitrogen atom bonded to X$_4$ and X$_5$. In one embodiment, X$_4$ and X$_5$, together with the nitrogen atom to which they are attached, form wherein the nitrogen atom is the nitrogen atom bonded to $X_4$ and $X_5$.

In one embodiment, m is 1. In one embodiment, m is 2. In one embodiment, m is 3.

Any of the substituent groups described above for any of $X_1$, $X_4$, $X_5$, $X_8$, $X_9$, and m can be combined with any of the substituent groups described above for one or more of the remainder of $X_1$, $X_4$, $X_5$, $X_8$, $X_9$, and m.

(1a) In one embodiment, $X_4$ is $C_1$-$C_4$ alkyl, and $X_5$ is phenyl-$(CX_8X_8)_m$. In one embodiment, the phenyl is optionally substituted with one or more substituents independently selected from deuterium, F, $SF_5$, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $C_1$-$C_4$ alkyl substituted with one or more F (e.g., methyl, ethyl, propyl, i-propyl, butyl, i-butyl, or t-butyl, each of which is substituted with one or more F), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $SF_5$, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, the phenyl is substituted with one or more substituents independently selected from F, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, the phenyl is substituted with one or more groups independently selected from F, $CF_3$, $CHF_2$, $CH_2F$, $OCF_3$, $OCHF_2$, and $OCH_2F$. In one embodiment, the phenyl is substituted with one or more substituents independently selected from F, $CF_3$, and $OCF_3$. In one embodiment, the phenyl is substituted with one or more substituents independently selected from F and $C_1$-$C_4$ alkyl substituted with one or more F (e.g., methyl, ethyl, propyl, i-propyl, butyl, i-butyl, or t-butyl, each of which is substituted with one or more F). In one embodiment, the phenyl is substituted with one or more substituents independently selected from F, $SF_5$, $CF_3$, $CHF_2$, $CH_2F$, $CH_2CF_3$, $CH_2CHF_2$, and $CH_2CH_2F$. In one embodiment, the phenyl is substituted with one or more substituents independently selected from F, $CF_3$, $CHF_2$, $CH_2F$, $CH_2CF_3$, $CH_2CHF_2$, and $CH_2CH_2F$. In one embodiment, the phenyl is substituted with one or more groups independently selected from F, $CF_3$, $CHF_2$, and $CH_2F$. In one embodiment, the phenyl is substituted with one or more substituents independently selected from F and $CF_3$. In one embodiment, the phenyl is substituted with one or more substituents independently selected from F and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $SF_5$, $OCF_3$, $OCHF_2$, $OCH_2F$, $OCH_2CF_3$, $OCH_2CHF_2$, and $OCH_2CH_2F$. In one embodiment, the phenyl is substituted with one or more substituents independently selected from F, $OCF_3$, $OCHF_2$, $OCH_2F$, $OCH_2CF_3$, $OCH_2CHF_2$, and $OCH_2CH_2F$. In one embodiment, the phenyl is substituted with one or more groups independently selected from F, $CF_3$, $CHF_2$, $CH_2F$, $OCF_3$, $OCHF_2$, and $OCH_2F$. In one embodiment, the phenyl is substituted with one or more substituents independently selected from F and $OCF_3$. In one embodiment, the phenyl is substituted with one or more substituents independently selected from $C_1$-$C_4$ alkyl (e.g., methyl, ethyl, propyl, i-propyl, butyl, i-butyl, or t-butyl) and $C_1$-$C_4$ alkoxy (e.g., methoxy, ethoxy, propoxy, i-propoxy, butoxy, i-butoxy, or t-butoxy). In one embodiment, the phenyl is substituted with one or more substituents independently selected from $CH_3$, $CH_2CH_3$, $OCH_3$, and $OCH_2CH_3$. In one embodiment, the phenyl is substituted with one or more substituents independently selected from $CH_3$ and $CH_2CH_3$. In one embodiment, the phenyl is substituted with one or more $CH_3$. In one embodiment, the phenyl is substituted with one or more substituents independently selected from $OCH_3$ and $OCH_2CH_3$. In one embodiment, the phenyl is substituted with one or more $OCH_3$.

(1b) In one embodiment, $X_4$ is $C_2$-$C_6$ alkenyl, and $X_5$ is phenyl-$(CX_8X_8)_m$. In one embodiment, the phenyl is optionally substituted with one or more substituents independently selected from deuterium, F, $SF_5$, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $C_1$-$C_4$ alkyl substituted with one or more F (e.g., methyl, ethyl, propyl, i-propyl, butyl, i-butyl, or t-butyl, each of which is substituted with one or more F), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $SF_5$, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, the phenyl is substituted with one or more substituents independently selected from F, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, the phenyl is substituted with one or more groups independently selected from F, $CF_3$, $CHF_2$, $CH_2F$, $OCF_3$, $OCHF_2$, and $OCH_2F$. In one embodiment, the phenyl is substituted with one or more substituents independently selected from F, $CF_3$, and $OCF_3$. In one embodiment, the phenyl is substituted with one or more substituents independently selected from F and $C_1$-$C_4$ alkyl substituted with one or more F (e.g., methyl, ethyl, propyl, i-propyl, butyl, i-butyl, or t-butyl, each of which is substituted with one or more F). In one embodiment, the phenyl is substituted with one or more substituents independently selected from F, $SF_5$, $CF_3$, $CHF_2$, $CH_2F$, $CH_2CF_3$, $CH_2CHF_2$, and $CH_2CH_2F$. In one embodiment, the phenyl is substituted with one or more substituents independently selected from F, $CF_3$, $CHF_2$, $CH_2F$, $CH_2CF_3$, $CH_2CHF_2$, and $CH_2CH_2F$. In one embodiment, the phenyl is substituted with one or more groups independently selected from F, $CF_3$, $CHF_2$, and $CH_2F$. In one embodiment, the phenyl is substituted with one or more substituents independently selected from F and $CF_3$. In one embodiment, the phenyl is substituted with one or more substituents independently selected from F and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $SF_5$, $OCF_3$, $OCHF_2$, $OCH_2F$, $OCH_2CF_3$, $OCH_2CHF_2$, and $OCH_2CH_2F$. In one embodiment, the phenyl is substituted with one or more substituents independently selected from F, $OCF_3$, $OCHF_2$, $OCH_2F$, $OCH_2CF_3$, $OCH_2CHF_2$, and $OCH_2CH_2F$. In one embodiment, the phenyl is substituted with one or more groups independently selected from F, $CF_3$, $CHF_2$, $CH_2F$, $OCF_3$, $OCHF_2$, and $OCH_2F$. In one embodiment, the phenyl is substituted with one or more substituents independently selected from F and $OCF_3$. In one embodiment, the phenyl is substituted with one or more substituents independently selected from $C_1$-$C_4$ alkyl (e.g., methyl, ethyl, propyl, i-propyl, butyl, i-butyl, or t-butyl) and $C_1$-$C_4$ alkoxy (e.g., methoxy, ethoxy, propoxy, i-propoxy, butoxy, i-butoxy, or t-butoxy). In one embodiment, the phenyl is substituted with one or more substituents independently selected from $CH_3$, $CH_2CH_3$, $OCH_3$, and $OCH_2CH_3$. In one embodiment, the phenyl is substituted with one or more substituents independently selected from $CH_3$ and $CH_2CH_3$. In one embodiment, the phenyl is substituted with one or more $CH_3$. In one embodiment, the phenyl is substituted with one or more substituents independently selected from $OCH_3$ and $OCH_2CH_3$. In one embodiment, the phenyl is substituted with one or more $OCH_3$.

(1c) In one embodiment, $X_4$ is $C_2$-$C_6$ alkynyl, and $X_5$ is phenyl-$(CX_8X_8)_m$. In one embodiment, the phenyl is optionally substituted with one or more substituents independently selected from deuterium, F, $SF_5$, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $C_1$-$C_4$ alkyl substituted with one or more F (e.g., methyl, ethyl, propyl, i-propyl, butyl, i-butyl, or t-butyl, each of which is substituted with one or more F), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $SF_5$, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, the phenyl is substituted with one or more substituents independently selected from F, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, the phenyl is substituted with one or more groups independently selected from F, $CF_3$, $CHF_2$, $CH_2F$, $OCF_3$, $OCHF_2$, and $OCH_2F$. In one embodiment, the phenyl is substituted with one or more substituents independently selected from F, $CF_3$, and $OCF_3$. In one embodiments, the phenyl is substituted with one or more substituents independently selected from F and $C_1$-$C_4$ alkyl substituted with one or more F (e.g., methyl, ethyl, propyl, i-propyl, butyl, i-butyl, or t-butyl, each of which is substituted with one or more F). In one embodiment, the phenyl is substituted with one or more substituents independently selected from F, SF$_5$, CF$_3$, CHF$_2$, CH$_2$F, CH$_2$CF$_3$, CH$_2$CHF$_2$, and CH$_2$CH$_2$F. In one embodiment, the phenyl is substituted with one or more substituents independently selected from F, CF$_3$, CHF$_2$, CH$_2$F, CH$_2$CF$_3$, CH$_2$CHF$_2$, and CH$_2$CH$_2$F. In one embodiment, the phenyl is substituted with one or more groups independently selected from F, CF$_3$, CHF$_2$, and CH$_2$F. In one embodiment, the phenyl is substituted with one or more substituents independently selected from F and CF$_3$. In one embodiment, the phenyl is substituted with one or more substituents independently selected from F and C$_1$-C$_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, SF$_5$, OCF$_3$, OCHF$_2$, OCH$_2$F, OCH$_2$CF$_3$, OCH$_2$CHF$_2$, and OCH$_2$CH$_2$F. In one embodiment, the phenyl is substituted with one or more substituents independently selected from F, OCF$_3$, OCHF$_2$, OCH$_2$F, OCH$_2$CF$_3$, OCH$_2$CHF$_2$, and OCH$_2$CH$_2$F. In one embodiment, the phenyl is substituted with one or more groups independently selected from F, CF$_3$, CHF$_2$, CH$_2$F, OCF$_3$, OCHF$_2$, and OCH$_2$F. In one embodiment, the phenyl is substituted with one or more substituents independently selected from F and OCF$_3$. In one embodiment, the phenyl is substituted with one or more substituents independently selected from C$_1$-C$_4$ alkyl (e.g., methyl, ethyl, propyl, i-propyl, butyl, i-butyl, or t-butyl) and C$_1$-C$_4$ alkoxy (e.g., methoxy, ethoxy, propoxy, i-propoxy, butoxy, i-butoxy, or t-butoxy). In one embodiment, the phenyl is substituted with one or more substituents independently selected from CH$_3$, CH$_2$CH$_3$, OCH$_3$, and OCH$_2$CH$_3$. In one embodiment, the phenyl is substituted with one or more substituents independently selected from CH$_3$ and CH$_2$CH$_3$. In one embodiment, the phenyl is substituted with one or more CH$_3$. In one embodiment, the phenyl is substituted with one or more substituents independently selected from OCH$_3$ and OCH$_2$CH$_3$. In one embodiment, the phenyl is substituted with one or more OCH$_3$.

(1d) In one embodiment, $X_4$ and $X_5$, together with the nitrogen atom to which they are attached, form a 5- to 7-membered heterocyclic ring comprising 1 to 2 heteroatoms selected from N, O, and S, optionally substituted with one or more substituents independently selected from deuterium, F, SF$_5$, C$_1$-C$_4$ alkyl (e.g., methyl, ethyl, propyl, i-propyl, butyl, i-butyl, or t-butyl), C$_1$-C$_4$ alkyl substituted with one or more F (e.g., methyl, ethyl, propyl, i-propyl, butyl, i-butyl, or t-butyl, each of which is substituted with one or more F), C$_1$-C$_4$ alkoxy (e.g., methoxy, ethoxy, propoxy, i-propoxy, butoxy, i-butoxy, or t-butoxy), and C$_1$-C$_4$ alkoxy substituted with one or more F (e.g., methoxy, ethoxy, propoxy, i-propoxy, butoxy, i-butoxy, or t-butoxy, each of which is substituted with one or more F). In one embodiment, the heterocyclic ring is substituted with one or more substituents independently selected from F, C$_1$-C$_4$ alkyl (e.g., methyl, ethyl, propyl, i-propyl, butyl, i-butyl, or t-butyl), C$_1$-C$_4$ alkyl substituted with one or more F (e.g., methyl, ethyl, propyl, i-propyl, butyl, i-butyl, or t-butyl, each of which is substituted with one or more F), C$_1$-C$_4$ alkoxy (e.g., methoxy, ethoxy, propoxy, i-propoxy, butoxy, i-butoxy, or t-butoxy), and C$_1$-C$_4$ alkoxy substituted with one or more F (e.g., methoxy, ethoxy, propoxy, i-propoxy, butoxy, i-butoxy, or t-butoxy, each of which is substituted with one or more F). In one embodiment, the heterocyclic ring is substituted with one or more substituents independently selected from F, C$_1$-C$_4$ alkyl substituted with one or more F (e.g., methyl, ethyl, propyl, i-propyl, butyl, i-butyl, or t-butyl, each of which is substituted with one or more F). In one embodiment, the heterocyclic ring is substituted with one or more substituents independently selected from F, C$_1$-C$_4$ alkyl substituted with one or more F (e.g., methyl, ethyl, propyl, i-propyl, butyl, i-butyl, or t-butyl, each of which is substituted with one or more F), and C$_1$-C$_4$ alkoxy substituted with one or more F (e.g., methoxy, ethoxy, propoxy, i-propoxy, butoxy, i-butoxy, or t-butoxy, each of which is substituted with one or more F). In one embodiment, the heterocyclic ring is substituted with one or more substituents independently selected from F, SF$_5$, CF$_3$, CHF$_2$, CH$_2$F, CH$_2$CF$_3$, CH$_2$CHF$_2$, CH$_2$CH$_2$F, OCF$_3$, OCHF$_2$, OCH$_2$F, OCH$_2$CF$_3$, OCH$_2$CHF$_2$, and OCH$_2$CH$_2$F. In one embodiment, the heterocyclic ring is substituted with one or more substituents independently selected from F, CF$_3$, CHF$_2$, CH$_2$F, CH$_2$CF$_3$, CH$_2$CHF$_2$, CH$_2$CH$_2$F, OCF$_3$, OCHF$_2$, OCH$_2$F, OCH$_2$CF$_3$, OCH$_2$CHF$_2$, and OCH$_2$CH$_2$F. In one embodiment, the heterocyclic ring is substituted with one or more groups independently selected from F, CF$_3$, CHF$_2$, CH$_2$F, OCF$_3$, OCHF$_2$, and OCH$_2$F. In one embodiment, the heterocyclic ring is substituted with one or more substituents independently selected from F, CF$_3$, and OCF$_3$. In one embodiment, the heterocyclic ring is substituted with one or more substituents independently selected from F and C$_1$-C$_4$ alkyl substituted with one or more F (e.g., methyl, ethyl, propyl, i-propyl, butyl, i-butyl, or t-butyl, each of which is substituted with one or more F). In one embodiment, the heterocyclic ring is substituted with one or more substituents independently selected from F, SF$_5$, CF$_3$, CHF$_2$, CH$_2$F, CH$_2$CF$_3$, CH$_2$CHF$_2$, and CH$_2$CH$_2$F. In one embodiment, the heterocyclic ring is substituted with one or more substituents independently selected from F, CF$_3$, CHF$_2$, CH$_2$F, CH$_2$CF$_3$, CH$_2$CHF$_2$, and CH$_2$CH$_2$F. In one embodiment, the heterocyclic ring is substituted with one or more groups independently selected from F, CF$_3$, CHF$_2$, and CH$_2$F. In one embodiment, the heterocyclic ring is substituted with one or more substituents independently selected from F and CF$_3$. In one embodiment, the heterocyclic ring is substituted with one or more substituents independently selected from F and C$_1$-C$_4$ alkoxy substituted with one or more F (e.g., methoxy, ethoxy, propoxy, i-propoxy, butoxy, i-butoxy, or t-butoxy, each of which is substituted with one or more F). In one embodiment, the heterocyclic ring is substituted with one or more substituents independently selected from F, SF$_5$, OCF$_3$, OCHF$_2$, OCH$_2$F, OCH$_2$CF$_3$, OCH$_2$CHF$_2$, and OCH$_2$CH$_2$F. In one embodiment, the heterocyclic ring is substituted with one or more substituents independently selected from F, OCF$_3$, OCHF$_2$, OCH$_2$F, OCH$_2$CF$_3$, OCH$_2$CHF$_2$, and OCH$_2$CH$_2$F. In one embodiment, the heterocyclic ring is substituted with one or more groups independently selected from F, CF$_3$, CHF$_2$, CH$_2$F, OCF$_3$, OCHF$_2$, and OCH$_2$F. In one embodiment, the heterocyclic ring is substituted with one or more substituents independently selected from F and OCF$_3$.

In one embodiment, the heterocyclic ring is substituted with one or more substituents independently selected from C$_1$-C$_4$ alkyl (e.g., methyl, ethyl, propyl, i-propyl, butyl, i-butyl, or t-butyl) and C$_1$-C$_4$ alkoxy (e.g., methoxy, ethoxy, propoxy, i-propoxy, butoxy, i-butoxy, or t-butoxy). In one embodiment, the heterocyclic ring is substituted with one or more substituents independently selected from CH$_3$, $CH_2CH_3$, $OCH_3$, and $OCH_2CH_3$. In one embodiment, the heterocyclic ring is substituted with one or more substituents independently selected from $CH_3$ and $CH_2CH_3$. In one embodiment, the heterocyclic ring is substituted with one or more $CH_3$. In one embodiment, the heterocyclic ring is substituted with one or more substituents independently selected from $OCH_3$ and $OCH_2CH_3$. In one embodiment, the heterocyclic ring is substituted with one or more $OCH_3$.

(1e) In one embodiment, $X_4$ and $X_5$, together with the nitrogen atom to which they are attached, form a 5- to 7-membered heterocyclic ring substituted with two or more substituents, wherein two substituents attached to adjacent carbon atoms on the heterocyclic ring, together with the carbon atoms to which they are attached, form a phenyl optionally substituted with one or more substituents independently selected from deuterium, F, $SF_5$, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $C_1$-$C_4$ alkyl substituted with one or more F (e.g., methyl, ethyl, propyl, i-propyl, butyl, i-butyl, or t-butyl, each of which is substituted with one or more F), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $SF_5$, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, the phenyl is substituted with one or more substituents independently selected from F, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, the phenyl is substituted with one or more groups independently selected from F, $CF_3$, $CHF_2$, $CH_2F$, $OCF_3$, $OCHF_2$, and $OCH_2F$. In one embodiment, the phenyl is substituted with one or more substituents independently selected from F, $CF_3$, and $OCF_3$. In one embodiment, the phenyl is substituted with one or more substituents independently selected from F and $C_1$-$C_4$ alkyl substituted with one or more F (e.g., methyl, ethyl, propyl, i-propyl, butyl, i-butyl, or t-butyl, each of which is substituted with one or more F). In one embodiment, the phenyl is substituted with one or more substituents independently selected from F, $SF_5$, $CF_3$, $CHF_2$, $CH_2F$, $CH_2CF_3$, $CH_2CHF_2$, and $CH_2CH_2F$. In one embodiment, the phenyl is substituted with one or more substituents independently selected from F, $CF_3$, $CHF_2$, $CH_2F$, $CH_2CF_3$, $CH_2CHF_2$, and $CH_2CH_2F$. In one embodiment, the phenyl is substituted with one or more groups independently selected from F, $CF_3$, $CHF_2$, and $CH_2F$. In one embodiment, the phenyl is substituted with one or more substituents independently selected from F and $CF_3$. In one embodiment, the phenyl is substituted with one or more substituents independently selected from F and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, the phenyl is substituted with one or more substituents independently selected from F, $SF_5$, $OCF_3$, $OCHF_2$, $OCH_2F$, $OCH_2CF_3$, $OCH_2CHF_2$, and $OCH_2CH_2F$. In one embodiment, the phenyl is substituted with one or more substituents independently selected from F, $OCF_3$, $OCHF_2$, $OCH_2F$, $OCH_2CF_3$, $OCH_2CHF_2$, and $OCH_2CH_2F$. In one embodiment, the phenyl is substituted with one or more groups independently selected from F, $CF_3$, $CHF_2$, $CH_2F$, $OCF_3$, $OCHF_2$, and $OCH_2F$. In one embodiment, the phenyl is substituted with one or more substituents independently selected from F and $OCF_3$. In one embodiment, the phenyl is substituted with one or more substituents independently selected from $C_1$-$C_4$ alkyl (e.g., methyl, ethyl, propyl, i-propyl, butyl, i-butyl, or t-butyl) and $C_1$-$C_4$ alkoxy (e.g., methoxy, ethoxy, propoxy, i-propoxy, butoxy, i-butoxy, or t-butoxy). In one embodiment, the phenyl is substituted with one or more substituents independently selected from $CH_3$, $CH_2CH_3$, $OCH_3$, and $OCH_2CH_3$. In one embodiment, the phenyl is substituted with one or more substituents independently selected from $CH_3$ and $CH_2CH_3$. In one embodiment, the phenyl is substituted with one or more $CH_3$. In one embodiment, the phenyl is substituted with one or more substituents independently selected from $OCH_3$ and $OCH_2CH_3$. In one embodiment, the phenyl is substituted with one or more $OCH_3$.

(2a) In one embodiment, m is 1.
(2b) In one embodiment, m is 2.
(2c) In one embodiment, m is 3.
(3a) In one embodiment, each $X_8$ is H.
(3b) In one embodiment, at least one $X_8$ is deuterium.
(3c) In one embodiment, at least one $X_8$ is $C_1$-$C_4$ alkyl, $C_1$-$C_4$ alkyl substituted with one or more F, or F.
(4a) In one embodiment, $X_1$ is methyl, and $X_9$ is methyl.
(4b) In one embodiment, $X_1$ is methyl, and $X_9$ is ethyl.
(4c) In one embodiment, $X_1$ is ethyl, and $X_9$ is ethyl.
(A1a) In one embodiment, $X_4$ and $X_5$ are each as defined in (1a), and m is as defined in any one of (2a)-(2c). In a further embodiment, m is as defined in (2a).
(A1b) In one embodiment, $X_4$ and $X_5$ are each as defined in (1b), and m is as defined in any one of (2a)-(2c). In a further embodiment, m is as defined in (2a).
(A1c) In one embodiment, $X_4$ and $X_5$ are each as defined in (1c), and m is as defined in any one of (2a)-(2c). In a further embodiment, m is as defined in (2a).
(A1d) In one embodiment, $X_4$ and $X_5$ are each as defined in (1d), and m is as defined in any one of (2a)-(2c). In a further embodiment, m is as defined in (2a).
(A1e) In one embodiment, $X_4$ and $X_5$ are each as defined in (1e), and m is as defined in any one of (2a)-(2c). In a further embodiment, m is as defined in (2a).

(B1a) In one embodiment, $X_4$, $X_5$, and m are each as defined in any one of (A1a)-(A1e), and $X_8$ is as defined in (3a).

(B1b) In one embodiment, $X_4$, $X_5$, and m are each as defined in any one of (A1a)-(A1e), and $X_8$ is as defined in (3b).

(B1c) In one embodiment, $X_4$, $X_5$, and m are each as defined in any one of (A1a)-(A1e), and $X_8$ is as defined in (3c).

(C1a) In one embodiment, $X_4$, $X_5$, $X_8$, and m are each as defined in any one of (B1a)-(B1c), and $X_1$ and $X_9$ are as defined in (4a).

(C1b) In one embodiment, $X_4$, $X_5$, $X_8$, and m are each as defined in any one of (B1a)-(B1c), and $X_1$ and $X_9$ are as defined in (4b).

(C1c) In one embodiment, $X_4$, $X_5$, $X_8$, and m are each as defined in any one of (B1a)-(B1c), and $X_1$ and $X_9$ are as defined in (4c).

In one embodiment, the compound of formula A is of formula IIa or IIb:

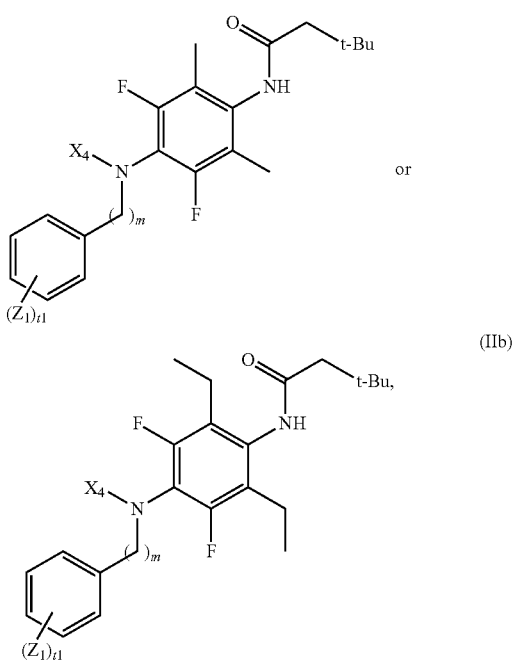

or a pharmaceutically acceptable salt or solvate thereof, wherein:

$X_4$ and m are each as defined above in formula A;

t1 is 1, 2, 3, 4, or 5; and each $Z_1$ is independently deuterium, F, $SF_5$, $C_1$-$C_4$ alkyl, $C_1$-$C_4$ alkyl substituted with one or more F, $C_1$-$C_4$ alkoxy, or $C_1$-$C_4$ alkoxy substituted with one or more F.

For a compound of formula IIa or IIb, t1 and $Z_1$ can each be, where applicable, selected from the groups described herein below, and any group described herein for any of t1 and $Z_1$ can be combined, where applicable, with any group described herein for the remainder of t1 and $Z_1$.

In one embodiment, t1 is 1, 2, or 3. In one embodiment, t1 is 1 or 2. In one embodiment, t1 is 1. In one embodiment, t1 is 2. In one embodiment, t1 is 3. In one embodiment, t1 is 4. In one embodiment, t1 is 5.

In one embodiment, at least one $Z_1$ is selected from deuterium, F, $SF_5$, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, at least one $Z_1$ is selected from F, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, at least one $Z_1$ is selected from $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, at least one $Z_1$ is selected from F, $C_1$-$C_4$ alkyl substituted with one or more F (e.g., methyl, ethyl, propyl, i-propyl, butyl, i-butyl, or t-butyl, each of which is substituted with one or more F), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, at least one $Z_1$ is selected from F, $SF_5$, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, at least one $Z_1$ is selected from F, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, at least one $Z_1$ is selected from F, $CF_3$, $CHF_2$, $CH_2F$, $OCF_3$, $OCHF_2$, and $OCH_2F$. In one embodiment, at least one $Z_1$ is selected from F, $CF_3$, and $OCF_3$. In one embodiment, at least one $Z_1$ is selected from F and $C_1$-$C_4$ alkyl substituted with one or more F (e.g., methyl, ethyl, propyl, i-propyl, butyl, i-butyl, or t-butyl, each of which is substituted with one or more F). In one embodiment, at least one $Z_1$ is selected from F, $SF_5$, $CF_3$, $CHF_2$, $CH_2F$, $CH_2CF_3$, $CH_2CHF_2$, and $CH_2CH_2F$. In one embodiment, at least one $Z_1$ is selected from F, $CF_3$, $CHF_2$, $CH_2F$, $CH_2CF_3$, $CH_2CHF_2$, and $CH_2CH_2F$. In one embodiment, at least one $Z_1$ is selected from F, $CF_3$, $CHF_2$, and $CH_2F$. In one embodiment, the phenyl is substituted with one or more substituents independently selected from F and $CF_3$. In one embodiment, at least one $Z_1$ is selected from F and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, at least one $Z_1$ is selected from F, $SF_5$, $OCF_3$, $OCHF_2$, $OCH_2F$, $OCH_2CF_3$, $OCH_2CHF_2$, and OCH$_2$CH$_2$F. In one embodiment, at least one $Z_1$ is selected from F, OCF$_3$, OCHF$_2$, OCH$_2$F, OCH$_2$CF$_3$, OCH$_2$CHF$_2$, and OCH$_2$CH$_2$F. In one embodiment, at least one $Z_1$ is selected from F, CF$_3$, CHF$_2$, CH$_2$F, OCF$_3$, OCHF$_2$, and OCH$_2$F. In one embodiment, at least one $Z_1$ is selected from F and OCF$_3$. In one embodiment, at least one $Z_1$ is F. In one embodiment, at least one $Z_1$ is CF$_3$. In one embodiment, at least one $Z_1$ is OCF$_3$. In one embodiment, at least one $Z_1$ is selected from C$_1$-C$_4$ alkyl (e.g., methyl, ethyl, propyl, i-propyl, butyl, i-butyl, or t-butyl) and C$_1$-C$_4$ alkoxy (e.g., methoxy, ethoxy, propoxy, i-propoxy, butoxy, i-butoxy, or t-butoxy). In one embodiment, at least one $Z_1$ is selected from CH$_3$, CH$_2$CH$_3$, OCH$_3$, and OCH$_2$CH$_3$. In one embodiment, at least one $Z_1$ is selected from CH$_3$ and CH$_2$CH$_3$. In one embodiment, at least one $Z_1$ is CH$_3$. In one embodiment, at least one $Z_1$ is selected from OCH$_3$ and OCH$_2$CH$_3$. In one embodiment, at least one $Z_1$ is OCH$_3$.

For a compound of formula IIa or IIb, $X_4$ and m can each be selected from any of the substituents described above in formula A, and any of the substituents described above for any of $X_4$ and m can be combined with any of the substituents described above for one or more of the remainder of $X_4$ and m, and can further be combined with any of the substituents described for any of t1 and $Z_1$.

In one embodiment, t1 is 1, and $Z_1$ is F, CF$_3$, or OCF$_3$. In one embodiment, t1 is 1, and $Z_1$ is F. In one embodiment, t1 is 1, and $Z_1$ is CF$_3$. In one embodiment, t1 is 1, and $Z_1$ is OCF$_3$.

In one embodiment, t1 is 1, $Z_1$ is F, CF$_3$, or OCF$_3$, and m is 1. In one embodiment, t1 is 1, $Z_1$ is F, and m is 1. In one embodiment, t1 is 1, $Z_1$ is CF$_3$, and m is 1. In one embodiment, t1 is 1, $Z_1$ is OCF$_3$, and m is 1.

In one embodiment, t1 is 1, $Z_1$ is F, CF$_3$, or OCF$_3$, m is 1, and $X_4$ is H. In one embodiment, t1 is 1, $Z_1$ is F, m is 1, and $X_4$ is H. In one embodiment, t1 is 1, $Z_1$ is CF$_3$, m is 1, and $X_4$ is H. In one embodiment, t1 is 1, $Z_1$ is OCF$_3$, m is 1, and $X_4$ is H.

In one embodiment, t1 is 1, and $Z_1$ is CH$_3$ or OCH$_3$. In one embodiment, t1 is 1, and $Z_1$ is CH$_3$. In one embodiment, t1 is 1, and $Z_1$ is OCH$_3$.

In one embodiment, t1 is 1, and $Z_1$ is CH$_3$ or OCH$_3$, and m is 1. In one embodiment, t1 is 1, and $Z_1$ is CH$_3$, and m is 1. In one embodiment, t1 is 1, and $Z_1$ is OCH$_3$, and m is 1.

In one embodiment, t1 is 1, and $Z_1$ is CH$_3$ or OCH$_3$, m is 1, and $X_4$ is H. In one embodiment, t1 is 1, and $Z_1$ is CH$_3$, m is 1, and $X_4$ is H. In one embodiment, t1 is 1, and $Z_1$ is OCH$_3$, m is 1, and $X_4$ is H.

In one embodiment, the compound of formula A is of formula IIIa or IIIb:

(IIIa)

or (IIIb)

or a pharmaceutically acceptable salt or solvate thereof, wherein:

q is 1, 2, or 3;

t2 is 1, 2, 3, or 4; and each $Z_2$ is independently deuterium, F, SF$_5$, C$_1$-C$_4$ alkyl, C$_1$-C$_4$ alkyl substituted with one or more F, C$_1$-C$_4$ alkoxy, or C$_1$-C$_4$ alkoxy substituted with one or more F.

For a compound of formula IIIa or IIIb, q, t2 and $Z_2$ can each be, where applicable, selected from the groups described herein below, and any group described herein for any of q, t2 and $Z_2$ can be combined, where applicable, with any group described herein for the remainder of q, t2 and $Z_2$.

In one embodiment, q is 1. In one embodiment, q is 2. In one embodiment, q is 3.

In one embodiment, t2 is 1. In one embodiment, t2 is 2. In one embodiment, t2 is 3. In one embodiment, t2 is 4.

In one embodiment, at least one $Z_2$ is selected from deuterium, F, SF$_5$, C$_1$-C$_4$ alkyl (e.g., methyl, ethyl, propyl, i-propyl, butyl, i-butyl, or t-butyl), C$_1$-C$_4$ alkyl substituted with one or more F (e.g., methyl, ethyl, propyl, i-propyl, butyl, i-butyl, or t-butyl, each of which is substituted with one or more F), C$_1$-C$_4$ alkoxy (e.g., methoxy, ethoxy, propoxy, i-propoxy, butoxy, i-butoxy, or t-butoxy), and C$_1$-C$_4$ alkoxy substituted with one or more F (e.g., methoxy, ethoxy, propoxy, i-propoxy, butoxy, i-butoxy, or t-butoxy, each of which is substituted with one or more F). In one embodiment, at least one $Z_2$ is selected from F, C$_1$-C$_4$ alkyl (e.g., methyl, ethyl, propyl, i-propyl, butyl, i-butyl, or t-butyl), C$_1$-C$_4$ alkyl substituted with one or more F (e.g., methyl, ethyl, propyl, i-propyl, butyl, i-butyl, or t-butyl, each of which is substituted with one or more F), C$_1$-C$_4$ alkoxy (e.g., methoxy, ethoxy, propoxy, i-propoxy, butoxy, i-butoxy, or t-butoxy), and C$_1$-C$_4$ alkoxy substituted with one or more F (e.g., methoxy, ethoxy, propoxy, i-propoxy, butoxy, i-butoxy, or t-butoxy, each of which is substituted with one or more F). In one embodiment, at least one $Z_2$ is selected from C$_1$-C$_4$ alkyl (e.g., methyl, ethyl, propyl, i-propyl, butyl, i-butyl, or t-butyl), C$_1$-C$_4$ alkyl substituted with one or more F (e.g., methyl, ethyl, propyl, i-propyl, butyl, i-butyl, or t-butyl, each of which is substituted with one or more F), C$_1$-C$_4$ alkoxy (e.g., methoxy, ethoxy, propoxy, i-propoxy, butoxy, i-butoxy, or t-butoxy), and C$_1$-C$_4$ alkoxy substituted with one or more F (e.g., methoxy, ethoxy, propoxy, i-propoxy, butoxy, i-butoxy, or t-butoxy, each of which is substituted with one or more F). In one embodiment, at least one $Z_2$ is selected from F, C$_1$-C$_4$ alkyl substituted with one or more F (e.g., methyl, ethyl, propyl, i-propyl, butyl, i-butyl, or t-butyl, each of which is substituted with one or more F), and C$_1$-C$_4$ alkoxy substituted with one or more F (e.g., methoxy, ethoxy, propoxy, i-propoxy, butoxy, i-butoxy, or t-butoxy, each of which is substituted with one or more F). In one embodiment, at least one $Z_2$ is selected from F, $SF_5$, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, at least one $Z_2$ is selected from F, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, at least one $Z_2$ is selected from F, $CF_3$, $CHF_2$, $CH_2F$, $OCF_3$, $OCHF_2$, and $OCH_2F$. In one embodiment, at least one $Z_2$ is selected from F, $CF_3$, and $OCF_3$. In one embodiment, at least one $Z_2$ is selected from F and $C_1$-$C_4$ alkyl substituted with one or more F (e.g., methyl, ethyl, propyl, i-propyl, butyl, i-butyl, or t-butyl, each of which is substituted with one or more F). In one embodiment, at least one $Z_2$ is selected from F, $SF_5$, $CF_3$, $CHF_2$, $CH_2F$, $CH_2CF_3$, $CH_2CHF_2$, and $CH_2CH_2F$. In one embodiment, at least one $Z_2$ is selected from F, $CF_3$, $CHF_2$, $CH_2F$, $CH_2CF_3$, $CH_2CHF_2$, and $CH_2CH_2F$. In one embodiment, at least one $Z_2$ is selected from F, $CF_3$, $CHF_2$, and $CH_2F$. In one embodiment, the phenyl is substituted with one or more substituents independently selected from F and $CF_3$. In one embodiment, at least one $Z_2$ is selected from F and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, at least one $Z_2$ is selected from F, $SF_5$, $OCF_3$, $OCHF_2$, $OCH_2F$, $OCH_2CF_3$, $OCH_2CHF_2$, and $OCH_2CH_2F$. In one embodiment, at least one $Z_2$ is selected from F, $OCF_3$, $OCHF_2$, $OCH_2F$, $OCH_2CF_3$, $OCH_2CHF_2$, and $OCH_2CH_2F$. In one embodiment, at least one $Z_2$ is selected from F, $CF_3$, $CHF_2$, $CH_2F$, $OCF_3$, $OCHF_2$, and $OCH_2F$. In one embodiment, at least one $Z_2$ is selected from F and $OCF_3$. In one embodiment, at least one $Z_2$ is F. In one embodiment, at least one $Z_2$ is $CF_3$. In one embodiment, at least one $Z_2$ is $OCF_3$. In one embodiment, at least one $Z_2$ is selected from $C_1$-$C_4$ alkyl (e.g., methyl, ethyl, propyl, i-propyl, butyl, i-butyl, or t-butyl) and $C_1$-$C_4$ alkoxy (e.g., methoxy, ethoxy, propoxy, i-propoxy, butoxy, i-butoxy, or t-butoxy). In one embodiment, at least one $Z_2$ is selected from $CH_3$, $CH_2CH_3$, $OCH_3$, and $OCH_2CH_3$. In one embodiment, at least one $Z_2$ is selected from $CH_3$ and $CH_2CH_3$. In one embodiment, at least one $Z_2$ is $CH_3$. In one embodiment, at least one $Z_2$ is selected from $OCH_3$ and $OCH_2CH_3$. In one embodiment, at least one $Z_2$ is $OCH_3$.

In one embodiment, the compound of formula A is of formula IVa or IVb:

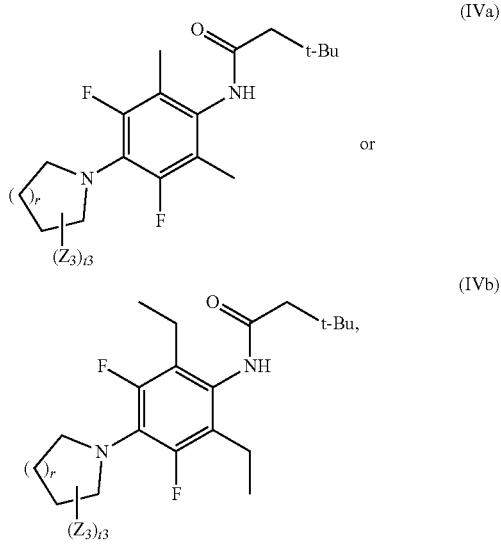

or a pharmaceutically acceptable salt or solvate thereof, wherein:
r is 1, 2, or 3;
t3 is 1, 2, 3, or 4; and
each $Z_3$ is independently deuterium, F, $SF_5$, $C_1$-$C_4$ alkyl, $C_1$-$C_4$ alkyl substituted with one or more F, $C_1$-$C_4$ alkoxy, or $C_1$-$C_4$ alkoxy substituted with one or more F.

For a compound of formula IVa or IVb, r, t3 and $Z_3$ can each be, where applicable, selected from the groups described herein below, and any group described herein for any of q, t2 and $Z_3$ can be combined, where applicable, with any group described herein for the remainder of q, t2 and $Z_3$.

In one embodiment, r is 1. In one embodiment, r is 2. In one embodiment, r is 3.

In one embodiment, t3 is 1. In one embodiment, t3 is 2. In one embodiment, t3 is 3. In one embodiment, t3 is 4.

In one embodiment, at least one $Z_3$ is selected from deuterium, F, $SF_5$, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, at least one $Z_3$ is selected from F, $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, at least one $Z_3$ is selected from $C_1$-$C_4$ alkyl (e.g., methyl, ethyl, propyl, i-propyl, butyl, i-butyl, or t-butyl), $C_1$-$C_4$ alkyl substituted with one or more F (e.g., methyl, ethyl, propyl, i-propyl, butyl, i-butyl, or t-butyl, each of which is substituted with one or more F), $C_1$-$C_4$ alkoxy (e.g., methoxy, ethoxy, propoxy, i-propoxy, butoxy, i-butoxy, or t-butoxy), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, at least one $Z_3$ is selected from F, $C_1$-$C_4$ alkyl substituted with one or more F (e.g., methyl, ethyl, propyl, i-propyl, butyl, i-butyl, or t-butyl, each of which is substituted with one or more F), and $C_1$-$C_4$ alkoxy substituted with one or more F (e.g., methoxy, ethoxy, propoxy, i-propoxy, butoxy, i-butoxy, or t-butoxy, each of which is substituted with one or more F). In one embodiment, at least one $Z_3$ is selected from F, $SF_5$, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, at least one $Z_3$ is selected from F, $CF_3$, $CHF_2$, $CH_2F$, $CH_2CF_3$, $CH_2CHF_2$, $CH_2CH_2F$, $OCF_3$, $OCHF_2$, $OCH_2F$, $OCH_2CF_3$, $OCH_2CHF_2$, and $OCH_2CH_2F$. In one embodiment, at least one $Z_3$ is selected from F, $CF_3$, $CHF_2$, $CH_2F$, $OCF_3$, $OCHF_2$, and $OCH_2F$. In one embodiment, at least one $Z_3$ is selected from F, $CF_3$, and $OCF_3$. In one embodiment, at least one $Z_3$ is selected from F and $C_1$-$C_4$ alkyl substituted with one or more F (e.g., methyl, ethyl, propyl, i-propyl, butyl, i-butyl, or t-butyl, each of which is substituted with one or more F). In one embodiment, at least one $Z_3$ is selected from F, $SF_5$, $CF_3$, $CHF_2$, $CH_2F$, $CH_2CF_3$, $CH_2CHF_2$, and $CH_2CH_2F$. In one embodiment, at least one $Z_3$ is selected from F, $CF_3$, CHF$_2$, CH$_2$F, CH$_2$CF$_3$, CH$_2$CHF$_2$, and CH$_2$CH$_2$F. In one embodiment, at least one Z$_3$ is selected from F, CF$_3$, CHF$_2$, and CH$_2$F. In one embodiment, the phenyl is substituted with one or more substituents independently selected from F and CF$_3$. In one embodiment, at least one Z$_3$ is selected from F and C$_1$-C$_4$ alkoxy substituted with one or more F (e.g., methoxy, ethoxy, propoxy, i-propoxy, butoxy, i-butoxy, or t-butoxy, each of which is substituted with one or more F). In one embodiment, at least one Z$_3$ is selected from F, SF$_5$, OCF$_3$, OCHF$_2$, OCH$_2$F, OCH$_2$CF$_3$, OCH$_2$CHF$_2$, and OCH$_2$CH$_2$F. In one embodiment, at least one Z$_3$ is selected from F, OCF$_3$, OCHF$_2$, OCH$_2$F, OCH$_2$CF$_3$, OCH$_2$CHF$_2$, and OCH$_2$CH$_2$F. In one embodiment, at least one Z$_3$ is selected from F, CF$_3$, CHF$_2$, CH$_2$F, OCF$_3$, OCHF$_2$, and OCH$_2$F. In one embodiment, at least one Z$_3$ is selected from F and OCF$_3$. In one embodiment, at least one Z$_3$ is F. In one embodiment, at least one Z$_3$ is CH$_3$. In one embodiment, at least one Z$_3$ is CF$_3$. In one embodiment, at least one Z$_3$ is OCH$_3$. In one embodiment, at least one Z$_3$ is OCF$_3$. In one embodiment, at least one Z$_3$ is selected from C$_1$-C$_4$ alkyl (e.g., methyl, ethyl, propyl, i-propyl, butyl, i-butyl, or t-butyl) and C$_1$-C$_4$ alkoxy (e.g., methoxy, ethoxy, propoxy, i-propoxy, butoxy, i-butoxy, or t-butoxy). In one embodiment, at least one Z$_3$ is selected from CH$_3$, CH$_2$CH$_3$, OCH$_3$, and OCH$_2$CH$_3$. In one embodiment, at least one Z$_3$ is selected from CH$_3$ and CH$_2$CH$_3$. In one embodiment, at least one Z$_3$ is CH$_3$. In one embodiment, at least one Z$_3$ is selected from OCH$_3$ and OCH$_2$CH$_3$. In one embodiment, at least one Z$_3$ is OCH$_3$.

In one embodiment, a compound of the present application is selected from the compounds in Table 1.

TABLE 1

| Compound No. | Structure |
| --- | --- |
| 1 | 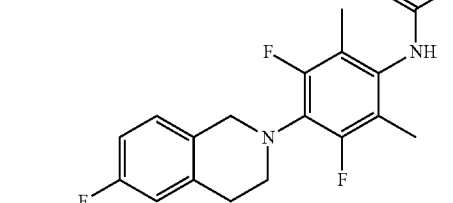 |
| 2 | 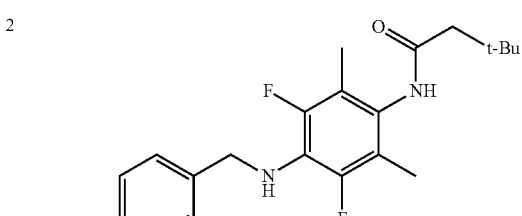 |
| 3 | 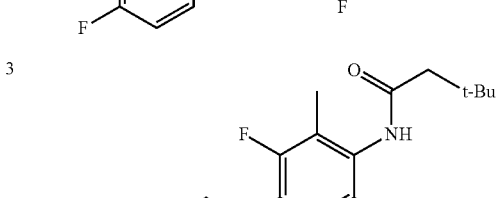 |
| 4 |  |
| 5 |  |
| 6 |  |

In one embodiment, a compound of the application is a pharmaceutically acceptable salt. In one embodiment, a compound of the application is a solvate. In one embodiment, a compound of the application is a hydrate.

A "selective KCNQ2/3 channel modulator" or "selective KCNQ2/3 channel opener" can be identified, for example, by comparing the ability of a compound to modulate KCNQ2/3 potassium channel (e.g., open KCNQ2/3 potassium channel) to its ability to modulate the other potassium channels (e.g., open other potassium channels). For example, a substance may be assayed for its ability to modulate KCNQ2/3 potassium channel, KCNQ3/5 potassium channel, KCNQ4 potassium channel, and/or other potassium channels (e.g., open KCNQ2/3 potassium channel, KCNQ3/5 potassium channel, KCNQ4 potassium channel, and/or other potassium channels). In some embodiments, the selectivity can be identified by measuring the EC$_{50}$ or IC$_{50}$ of the compounds.

In some embodiments, one or more of the compounds of the present application modulate KCNQ2/3 potassium channel more selectively over other potassium channels. In some embodiments, one or more of the compounds of the present application are about 10%, about 20%, about 30%, about 40%, about 50%, about 60%, about 70%, about 80%, about 90%, or about 99% more selective at modulating KCNQ2/3 potassium channel (e.g., opening KCNQ2/3 potassium channel) more selectively over other potassium channels (e.g., KCNQ3/5 potassium channel and/or KCNQ4 potassium channel). In some embodiments, one or more of the compounds of the present application are about 10%, about 20%, about 30%, about 40%, or about 50% more selective at modulating KCNQ2/3 potassium channel (e.g., opening KCNQ2/3 potassium channel) more selectively over other potassium channels (e.g., KCNQ3/5 potassium channel and/ or KCNQ4 potassium channel). In some embodiments, one or more of the compounds of the present application are about 20%, about 30%, about 40%, about 50%, or about 60% more selective at modulating KCNQ2/3 potassium channel (e.g., opening KCNQ2/3 potassium channel) more selectively over other potassium channels (e.g., KCNQ3/5 potassium channel and/or KCNQ4 potassium channel). In some embodiments, one or more of the compounds of the present application are about 30%, about 40%, about 50%, about 60%, or about 70% more selective at modulating KCNQ2/3 potassium channel (e.g., opening KCNQ2/3 potassium channel) more selectively over other potassium channels (e.g., KCNQ3/5 potassium channel and/or KCNQ4 potassium channel). In some embodiments, one or more of the compounds of the present application are about 40%, about 50%, about 60%, about 70%, or about 80% more selective at modulating KCNQ2/3 potassium channel (e.g., opening KCNQ2/3 potassium channel) more selectively over other potassium channels (e.g., KCNQ3/5 potassium channel and/or KCNQ4 potassium channel). In some embodiments, one or more of the compounds of the present application are about 50%, about 60%, about 70%, about 80%, or about 90% more selective at modulating KCNQ2/3 potassium channel (e.g., opening KCNQ2/3 potassium channel) more selectively over other potassium channels (e.g., KCNQ3/5 potassium channel and/or KCNQ4 potassium channel). In some embodiments, one or more of the compounds of the present application are about 60%, about 70%, about 80%, about 90%, or about 99% more selective at modulating KCNQ2/3 potassium channel (e.g., opening KCNQ2/3 potassium channel) more selectively over other potassium channels (e.g., KCNQ3/5 potassium channel and/or KCNQ4 potassium channel).

In some embodiments, one or more of the compounds of the present application are between about 10% and about 99% more selective more selective at modulating KCNQ2/3 potassium channel (e.g., open KCNQ2/3 potassium channel) more selectively over other potassium channels (e.g., KCNQ3/5 potassium channel and/or KCNQ4 potassium channel). In some embodiments, one or more of the compounds of the present application are between about 10% and about 30% more selective more selective at modulating KCNQ2/3 potassium channel (e.g., open KCNQ2/3 potassium channel) more selectively over other potassium channels (e.g., KCNQ3/5 potassium channel and/or KCNQ4 potassium channel). In some embodiments, one or more of the compounds of the present application are between about 20% and about 40% more selective more selective at modulating KCNQ2/3 potassium channel (e.g., open KCNQ2/3 potassium channel) more selectively over other potassium channels (e.g., KCNQ3/5 potassium channel and/or KCNQ4 potassium channel). In some embodiments, one or more of the compounds of the present application are between about 30% and about 50% more selective more selective at modulating KCNQ2/3 potassium channel (e.g., open KCNQ2/3 potassium channel) more selectively over other potassium channels (e.g., KCNQ3/5 potassium channel and/or KCNQ4 potassium channel). In some embodiments, one or more of the compounds of the present application are between about 40% and about 60% more selective more selective at modulating KCNQ2/3 potassium channel (e.g., open KCNQ2/3 potassium channel) more selectively over other potassium channels (e.g., KCNQ3/5 potassium channel and/or KCNQ4 potassium channel). In some embodiments, one or more of the compounds of the present application are between about 50% and about 70% more selective more selective at modulating KCNQ2/3 potassium channel (e.g., open KCNQ2/3 potassium channel) more selectively over other potassium channels (e.g., KCNQ3/5 potassium channel and/or KCNQ4 potassium channel). In some embodiments, one or more of the compounds of the present application are between about 60% and about 80% more selective more selective at modulating KCNQ2/3 potassium channel (e.g., open KCNQ2/3 potassium channel) more selectively over other potassium channels (e.g., KCNQ3/5 potassium channel and/or KCNQ4 potassium channel). In some embodiments, one or more of the compounds of the present application are between about 70% and about 90% more selective more selective at modulating KCNQ2/3 potassium channel (e.g., open KCNQ2/3 potassium channel) more selectively over other potassium channels (e.g., KCNQ3/5 potassium channel and/or KCNQ4 potassium channel). In some embodiments, one or more of the compounds of the present application are between about 80% and about 99% more selective more selective at modulating KCNQ2/3 potassium channel (e.g., open KCNQ2/3 potassium channel) more selectively over other potassium channels (e.g., KCNQ3/5 potassium channel and/or KCNQ4 potassium channel).

As used herein, "selective", "selective KCNQ2/3 channel modulator", "selective KCNQ2/3 channel opener", or "selective KCNQ2/3 compound" refers to a compound, e.g., a compound of the application, that effectively modulates KCNQ2/3 potassium channel (e.g., opens KCNQ2/3 potassium channel) to a greater extent than other potassium channels (e.g., KCNQ3/5 potassium channel and/or KCNQ4 potassium channel).

In some embodiments, the compounds of the application are KCNQ2/3 channel modulators that modulates KCNQ2/3 potassium channel (e.g., opens KCNQ2/3 potassium channel) with at least 2-fold, 3-fold, 5-fold, 10-fold, 25-fold, 50-fold or 100-fold selectivity over other potassium channels (e.g., KCNQ3/5 potassium channel and/or KCNQ4 potassium channel).

The present application relates to pharmaceutical compositions comprising one of the compounds of the application as an active ingredient. In one embodiment, the application provides a pharmaceutical composition comprising at least one compound disclosed herein (e.g., a compound of formula A, Ia, Ib, IIa, IIb, IIIa, IIIb, IVa, or IVb), or a pharmaceutically acceptable salt or solvate thereof, and one or more pharmaceutically acceptable carrier or excipient. In one embodiment, the application provides a pharmaceutical composition comprising at least one compound of Table 1, or a pharmaceutically acceptable salt or solvate thereof, and one or more pharmaceutically acceptable carrier or excipient.

The present application relates to a method of synthesizing a compound of the application or a pharmaceutically acceptable salt or solvate thereof. A compound of the application can be synthesized using a variety of methods known in the art, such as those described in U.S. Pat. No. 8,916,133, the contents of which are incorporated by reference in their entirety. The schemes and description below depict general routes for the preparation of a compound of the application. For example, compounds of the present application can be synthesized by following the steps outlined in Schemes 1-2 which comprise different sequences of assembling intermediates 1a-1e and 2a-2f. Starting materials are either commercially available or made by known procedures in the reported literature or as illustrated.

Scheme 1

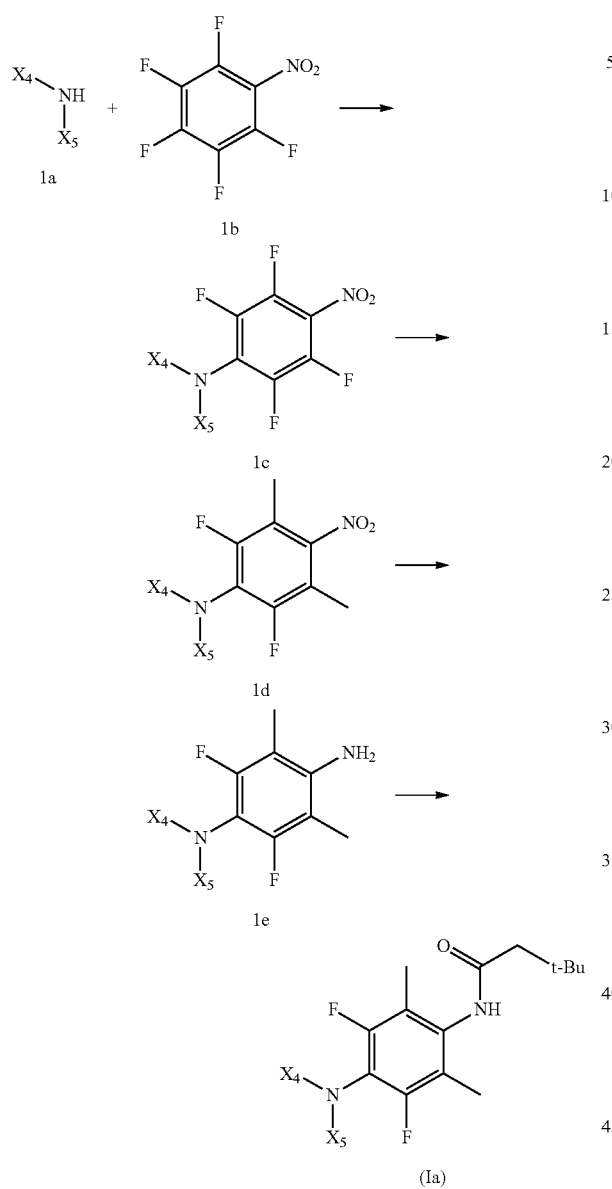

(Ia)

Scheme 2

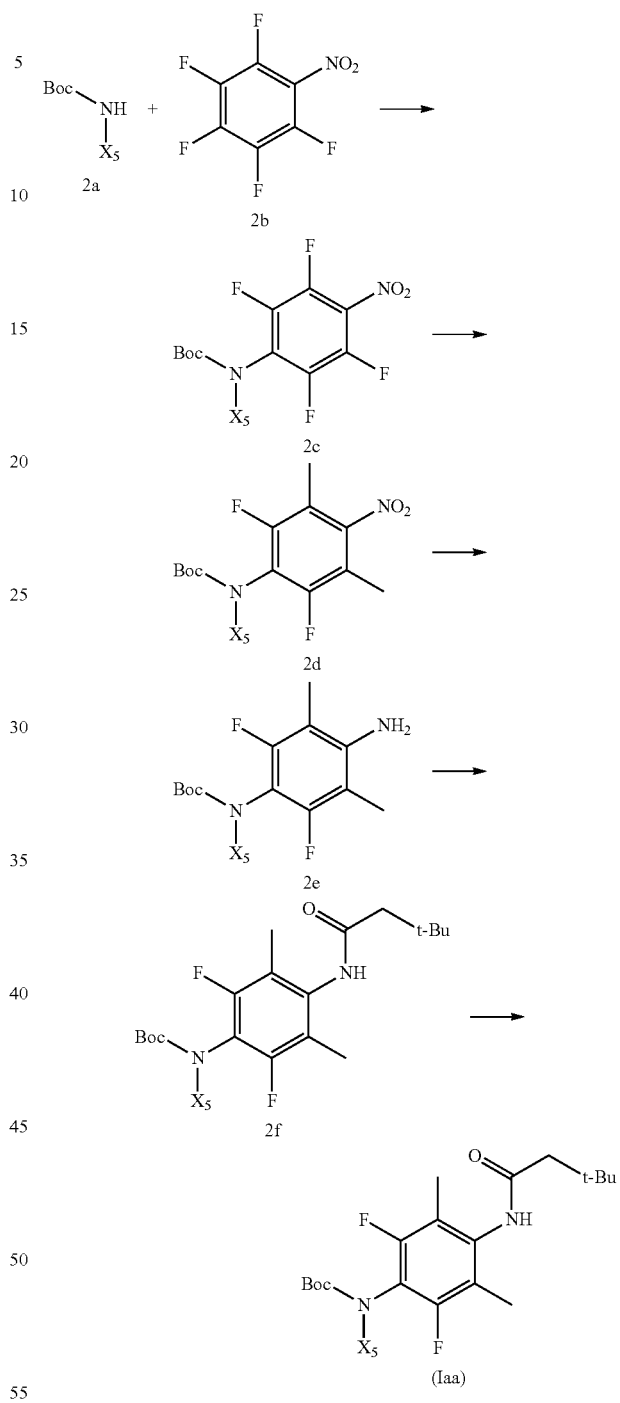

(Iaa)

The general way of preparing representative compounds of the present application using intermediates 1a-1e is outlined in Scheme 1. Nucleophilic addition of 1a to fluoride 1b in the presence of a base (e.g., triethylamine (Et$_3$N)) in a solvent (e.g., dimethylsulfoxide (DMSO)) and optionally at an elevated temperature provides intermediate 1c. Methylation of 1c with a base (e.g., sodium hydride (NaH)) and an alkyltriphenylphosphonium salt (e.g., methyltriphenylphosphonium bromide (MePPh$_3$Br)) in a solvent (e.g., tetrahydrofuran (THF)) and optionally at an elevated temperature provides intermediate 1d. Reduction of 1d using a metal catalyst (e.g., Zinc (Zn)) and ammonium chloride (NH$_4$Cl) in a solvent (e.g., methanol (MeOH) and water (H$_2$O)) and optionally at an elevated temperature provides intermediate 1e. Acetylation of 1e with tert-butylacetyl chloride in the presence of a base (e.g., diisopropylethylamine (DIPEA)) in a solvent (e.g., dichloromethane (DCM)) and optionally at an elevated temperature provides a compound of formula Ia.

The general way of preparing representative compounds of the present application using intermediates 2a-2f is outlined in Scheme 2. Nucleophilic addition of 2a to fluoride 2b in the presence of a base (e.g., triethylamine (Et$_3$N)) in a solvent (e.g., dimethylsulfoxide (DMSO)) and optionally at an elevated temperature provides intermediate 2c. Methylation of 2c with a base (e.g., sodium hydride (NaH)) and an alkyltriphenylphosphonium salt (e.g., methyltriphenylphosphonium bromide (MePPh$_3$Br)) in a solvent (e.g., tetrahydrofuran (THF)) and optionally at an elevated temperature provides intermediate 2d. Reduction of 2d using a metal catalyst (e.g., Zinc (Zn)) and ammonium chloride (NH₄Cl) in a solvent (e.g., methanol (MeOH) and water (H₂O)) and optionally at an elevated temperature provides intermediate 2e. Acetylation of 2e with tert-butylacetyl chloride in the presence of a base (e.g., diisopropylethylamine (DIPEA)) in a solvent (e.g., dichloromethane (DCM)) and optionally at an elevated temperature provides intermediate 2f. Deprotection of 2f in the presence of an acid (e.g., hydrochloric acid (HCl)) in a solvent (e.g., dichloromethane (DCM) and water (H₂O)) and optionally at an elevated temperature provides a compound of formula Iaa.

The present application also comprehends deuterium labeled compounds, wherein one or more hydrogen atoms is replaced by a deuterium atom having an abundance of deuterium at that position that is substantially greater than the natural abundance of deuterium, which is 0.015%.

Deuterium labeled compounds can be prepared by using any of a variety of art-recognized techniques. For example, deuterium labeled compounds of any of the formulae described herein and compounds listed in Table 1 of this application can be prepared.

In one aspect, a deuterium labeled compound of the application is a pharmaceutically acceptable salt. In one aspect, a deuterium labeled compound of the application is a solvate. In one aspect, a deuterium labeled compound of the application is a hydrate.

The present application relates to pharmaceutical compositions comprising one of the deuterium labeled compounds of the application as an active ingredient. In one aspect, the application provides a pharmaceutical composition comprising at least one deuterium labeled compound of any of the formulae described herein or a pharmaceutically acceptable salt or solvate thereof and one or more pharmaceutically acceptable carrier or excipient.

The present application relates to a method of synthesizing a deuterium labeled compound of the application or a pharmaceutically acceptable salt or solvate thereof. The deuterium labeled compounds of the application can be prepared using any of a variety of art-recognized techniques, such as those described in U.S. Pat. No. 8,916,133, the contents of which are incorporated by reference in their entirety. For example, a deuterium labeled compound can be prepared by starting with deuterium labeled Compound 1 and/or substituting a readily available deuterium labeled reagent for a non-deuterium labeled reagent.

The scheme and description below depicts a general route for the incorporation of deuterium label to produce a deuterium labeled compound of the application.

Scheme 1A

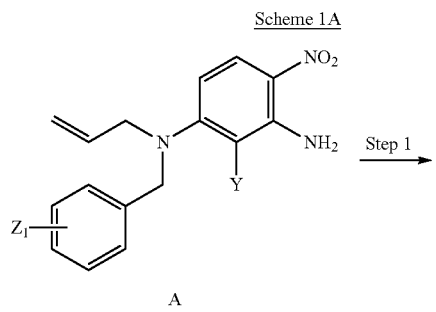

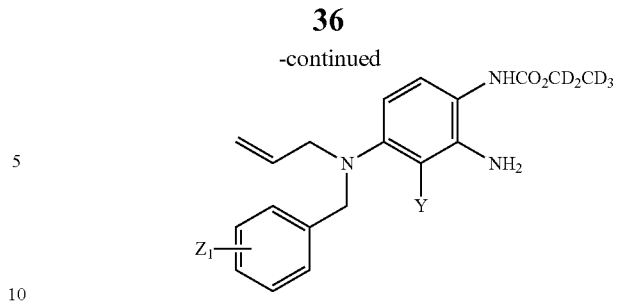

Scheme 1A outlines a preparation for a deuterium labeled compound of the application. The preparation begins with Compound A (from Scheme 1A described herein). In Step 1, the nitro group of Compound A is reduced and then the deuterium label is introduced via formation of a carbamate containing one or more deuterium. For example, the nitro group of Compound A can be reduced using zinc powder and ammonium chloride in methanol and the carbamate can be formed using ethyl-d₅ chloroformate to provide a deuterium labeled compound.

In some embodiments, temporary protecting groups may be used to prevent other reactive functionality, such as amines, thiols, alcohols, phenols, and carboxylic acids, from participating or interfering in the fluorination reaction. Representative amine protecting groups include, for example, tert-butoxycarbonyl and trityl (removed under acid conditions), Fmoc (removed by the use of secondary amines such as piperidine), and benzyloxycarbonyl (removed by strong acid or by catalytic hydrogenolysis). The trityl group may also be used for the protection of thiols, phenols, and alcohols. In certain embodiments the carboxylic acid protecting groups include, for example, tert-butyl ester (removed by mild acid), benzyl ester (usually removed by catalytic hydrogenolysis), and alkyl esters such as methyl or ethyl (usually removed by mild base). All protecting groups may be removed at the conclusion of the synthesis using the conditions described above for the individual protecting groups, and the final product may be purified by techniques which would be readily apparent to one of ordinary skill in the art, in combination with the teachings described herein.

Biological Assays

Assessment of KCNQ2/3 Channel Activation Activity

Biological activities of the compounds of the application can be assessed by using various methods known in the art. For example, the KCNQ2/3 channel activation activity of the compounds of the application can be evaluated through an in vitro assay described below.

The in vitro effects of a compound of the application on cloned KCNQ2/3 potassium channels (e.g., encoded by the human KCNQ2/3 gene) are evaluated using a patch clamp system. Compounds of the application are tested at various concentrations (e.g., 0.01, 0.1, 1, 10 and 100 μM) for a certain duration of exposure (e.g., 5 min). The baseline for each recording is established. A single test compound concentration is applied for a certain duration of exposure after the vehicle. Each recording ends with treatment with a supramaximal dose of linopirdine. The % activation is calculated using the following equation by using leak subtracted responses:

$$\frac{\text{vehicle\_response} - \text{compound\_response}}{\text{vehicle\_response} - \text{flupirtine\_response}}$$

Maximal Electroshock Seizure Test (MES)

In MES test, the ability of different doses of the test compound in preventing seizure induced by an electrical stimulus, delivered through the corneal electrodes primed with a drop of anesthetic/electrolyte solution is tested. Mice are restrained and released immediately following corneal stimulation that allows for the observation of the entire seizure episode. A maximal seizure in a test animal includes four distinct phases that includes, hind leg flexor component tonic phase (Phase I), hind leg extensor component of the tonic phase (Phase II), intermittent, whole-body clonus (Phase III), and muscular relaxation (Phase IV) followed by seizure termination (Woodbury & Davenport, 1952; Racine et al., 1972). Test compounds are tested for their ability to abolish hind limb tonic extensor component that indicates the compound's ability to inhibit MES-induced seizure spread. Compounds are pre-administered (i.p) and tested at various time points for the abolishment of hind limb tonic extensor component after electrical stimulus.

Corneal-Kindled Mouse Model of Partial Seizures

In corneal kindled seizure model, mice are kindled electrically with stimulation delivered through corneal electrodes primed with tetracaine hydrochloride in saline, twice daily, until 5 consecutive stage V seizures are induced. Mice are considered kindled when they display at least 5 consecutive stage V seizures according to the Racine scale (Racine et al., 1972) including, mouth and facial clonus (stage I), Stage I plus head nodding (Stage II), Stage II plus forelimb clonus (Stage III), Stage III plus rearing (Stage IV), and stage IV plus repeated rearing and falling (Stage V) (Racine et al., 1972). At the completion of the kindling acquisition, mice are permitted a 3-day stimulation-free period prior to any drug testing. On the day of the experiment, fully kindled mice are pre-administered (i.p) with increasing doses of the test compound and challenged with the corneal kindling stimulus. Mice are scored as protected (seizure score of <3) or not protected, (seizure score≥4) based on the Racine scoring (Racine et al., 1972).

Pharmaceutical Compositions

The present application relates to pharmaceutical compositions comprising a compound of the application as an active ingredient. In one embodiment, the application provides a pharmaceutical composition comprising at least one compound of each of the formulae described herein, or a pharmaceutically acceptable salt or solvate thereof, and one or more pharmaceutically acceptable carriers or excipients. In one embodiment, the application provides a pharmaceutical composition comprising at least one compound selected from Table 1.

As used herein, the term "composition" is intended to encompass a product comprising the specified ingredients in the specified amounts, as well as any product which results, directly or indirectly, from combination of the specified ingredients in the specified amounts.

The compounds of the application can be formulated for oral administration in forms such as tablets, capsules (each of which includes sustained release or timed release formulations), pills, powders, granules, elixirs, tinctures, suspensions, syrups and emulsions. The compounds of the application can also be formulated for intravenous (bolus or in-fusion), intraperitoneal, topical, subcutaneous, intramuscular or transdermal (e.g., patch) administration, all using forms well known to those of ordinary skill in the pharmaceutical arts.

The formulation of the present application may be in the form of an aqueous solution comprising an aqueous vehicle. The aqueous vehicle component may comprise water and at least one pharmaceutically acceptable excipient. Suitable acceptable excipients include those selected from the group consisting of a solubility enhancing agent, chelating agent, preservative, tonicity agent, viscosity/suspending agent, buffer, and pH modifying agent, and a mixture thereof.

Any suitable solubility enhancing agent can be used. Examples of a solubility enhancing agent include cyclodextrin, such as those selected from the group consisting of hydroxypropyl-β-cyclodextrin, methyl-β-cyclodextrin, randomly methylated-β-cyclodextrin, ethylated-β-cyclodextrin, triacetyl-β-cyclodextrin, peracetylated-β-cyclodextrin, carboxymethyl-β-cyclodextrin, hydroxyethyl-β-cyclodextrin, 2-hydroxy-3-(trimethylammonio)propyl-β-cyclodextrin, glucosyl-β-cyclodextrin, sulphated β-cyclodextrin (S-β-CD), maltosyl-β-cyclodextrin, β-cyclodextrin sulfobutyl ether, branched-β-cyclodextrin, hydroxypropyl-γ-cyclodextrin, randomly methylated-γ-cyclodextrin, and trimethyl-γ-cyclodextrin, and mixtures thereof.

Any suitable chelating agent can be used. Examples of a suitable chelating agent include those selected from the group consisting of ethylenediaminetetraacetic acid and metal salts thereof, disodium edetate, trisodium edetate, and tetrasodium edetate, and mixtures thereof.

Any suitable preservative can be used. Examples of a preservative include those selected from the group consisting of quaternary ammonium salts such as benzalkonium halides (preferably benzalkonium chloride), chlorhexidine gluconate, benzethonium chloride, cetyl pyridinium chloride, benzyl bromide, phenylmercury nitrate, phenylmercury acetate, phenylmercury neodecanoate, merthiolate, methylparaben, propylparaben, sorbic acid, potassium sorbate, sodium benzoate, sodium propionate, ethyl p-hydroxybenzoate, propylaminopropyl biguanide, and butyl-p-hydroxybenzoate, and sorbic acid, and mixtures thereof.

The aqueous vehicle may also include a tonicity agent to adjust the tonicity (osmotic pressure). The tonicity agent can be selected from the group consisting of a glycol (such as propylene glycol, diethylene glycol, triethylene glycol), glycerol, dextrose, glycerin, mannitol, potassium chloride, and sodium chloride, and a mixture thereof.

The aqueous vehicle may also contain a viscosity/suspending agent. Suitable viscosity/suspending agents include those selected from the group consisting of cellulose derivatives, such as methyl cellulose, ethyl cellulose, hydroxyethylcellulose, polyethylene glycols (such as polyethylene glycol 300, polyethylene glycol 400), carboxymethyl cellulose, hydroxypropylmethyl cellulose, and cross-linked acrylic acid polymers (carbomers), such as polymers of acrylic acid cross-linked with polyalkenyl ethers or divinyl glycol (Carbopols—such as Carbopol 934, Carbopol 934P, Carbopol 971, Carbopol 974 and Carbopol 974P), and a mixture thereof.

In order to adjust the formulation to an acceptable pH (typically a pH range of about 5.0 to about 9.0, more preferably about 5.5 to about 8.5, particularly about 6.0 to about 8.5, about 7.0 to about 8.5, about 7.2 to about 7.7, about 7.1 to about 7.9, or about 7.5 to about 8.0), the formulation may contain a pH modifying agent. The pH modifying agent is typically a mineral acid or metal hydroxide base, selected from the group of potassium hydroxide, sodium hydroxide, and hydrochloric acid, and mixtures thereof, and preferably sodium hydroxide and/or hydrochloric acid. These acidic and/or basic pH modifying agents are added to adjust the formulation to the target acceptable pH range. Hence it may not be necessary to use both acid and base—depending on the formulation, the addition of one of the acid or base may be sufficient to bring the mixture to the desired pH range.

The aqueous vehicle may also contain a buffering agent to stabilize the pH. When used, the buffer is selected from the group consisting of a phosphate buffer (such as sodium dihydrogen phosphate and disodium hydrogen phosphate), a borate buffer (such as boric acid, or salts thereof including disodium tetraborate), a citrate buffer (such as citric acid, or salts thereof including sodium citrate), and ε-aminocaproic acid, and mixtures thereof.

The formulation may further comprise a wetting agent. Suitable classes of wetting agents include those selected from the group consisting of polyoxypropylene-polyoxyethylene block copolymers (poloxamers), polyethoxylated ethers of castor oils, polyoxyethylenated sorbitan esters (polysorbates), polymers of oxyethylated octyl phenol (Tyloxapol), polyoxyl 40 stearate, fatty acid glycol esters, fatty acid glyceryl esters, sucrose fatty esters, and polyoxyethylene fatty esters, and mixtures thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Methods of Use

The present application relates to methods for the use of compounds of the application. The compounds of the application have a useful pharmacological activity spectrum and are therefore particularly suitable for the prophylaxis and/or treatment of diseases or disorders.

The present application provides a method of treating or preventing diseases or disorders, comprising administering a therapeutically effective amount of a compound of the application, or a pharmaceutically acceptable salt or solvate thereof, to a subject in need thereof. The present application also provides the use of a compound of the application, or a pharmaceutically acceptable salt or solvate thereof, for the preparation of a medicament for administration to a subject for the treatment or prevention of diseases or disorders. The present application also provides a compound of the application, or a pharmaceutically acceptable salt or solvate thereof, for treating or preventing diseases or disorders.

In one embodiment, the disease or disorder is a condition which can be ameliorated by KCNQ2/3 potassium channel opening. In one embodiment, the disease or disorder is selected from epilepsy, neurotransmission disorder, CNS disorder, neurodegenerative disease (e.g., Alzheimer's disease, ALS, motor neuron disease, Parkinson's disease, macular degeneration, or glaucoma), cognitive disorder (e.g., degenerative dementia (including senile dementia, Alzheimer's disease, Pick's disease, Huntington's chorea, Parkinson's disease, and Creutzfeldt-Jakob disease); vascular dementia (including multi-infarct dementia); dementia associated with intracranial space occupying lesions, trauma, infections or related conditions (including HIV infection), metabolism, toxins, anoxia, or vitamin deficiency; mild cognitive impairment associated with ageing, particularly Age Associated Memory Loss, or learning deficiencies), bipolar disorder (e.g., Type I or II bipolar disorder), unipolar depression, anxiety, migraine, ataxia, myokimia, tinnitus, functional bowel disorders (e.g., non-ulcer dyspepsia, non-cardiac chest pain, or irritable bowel syndrome), cancer, inflammatory disease, ophthalmic disease (e.g., retinitis, retinopathies, uveitis, or acute injury to the eye tissue), asthma, allergic rhinitis, respiratory distress syndrome, gastrointestinal conditions (e.g., inflammatory bowel disease, Chron's disease, gastritis, irritable bowel syndrome, or ulcerative colitis), and inflammation in such diseases as vascular disease, migraine, periarteritis nodosa, thyroiditis, aplastic anemia, Hodgkin's disease, sclerodoma, type I diabetes, myasthenia gravis, multiple sclerosis, sorcoidosis, nephrotic syndrome, Bechet's syndrome, polymyositis, gingivitis, conjunctivitis, and myocardial ischemia.

In one embodiment, the application provides a method of producing an anti-epileptic, muscle relaxing, fever reducing, peripherally analagesic, and/or anti-convulsive effect in a subject in need thereof, comprising administering to the subject an effective amount of a compound of the application, or a pharmaceutically acceptable salt or solvate thereof. The present application also provides the use of a compound of the application, or a pharmaceutically acceptable salt or solvate thereof, for the preparation of a medicament for administration to a subject for producing an anti-epileptic, muscle relaxing, fever reducing, peripherally analagesic, and/or anti-convulsive effect. The present application also provides a compound of the application, or a pharmaceutically acceptable salt or solvate thereof, for producing an anti-epileptic, muscle relaxing, fever reducing, peripherally analagesic, and/or anti-convulsive effect.

In one embodiment, the application provides compounds that are useful as an anti-convulsant. They are therefore useful in treating or preventing epilepsy. Compounds of the application may be used to improve the condition of a host, typically a human being, suffering from epilepsy. They may be employed to alleviate the symptoms of epilepsy in a host. "Epilepsy" is intended to include the following seizures: simple partial seizures, complex partial seizures, secondary generalized seizures, generalized seizures including absence seizures, myoclonic seizures, clonic seizures, tonic seizures, tonic clonic seizures and atonic seizures. Partial-onset seizures are the most common type of seizure in adult patients. For partial seizures, there is a focal epileptic zone (site of seizure onset), and seizure activity is initially limited to one hemisphere. Partial seizures can be further sub-divided into simple partial (without impairment of consciousness), complex partial (with impairment of consciousness with or following a simple partial onset) and secondarily generalized (i.e., partial seizures, either simple or complex, which evolve to generalized tonic-clonic seizures). Simple partial seizures, depending on the anatomical site of origin of the seizure, may have motor, somatosensory or special sensory, autonomic or psychic signs or symptoms.

In one embodiment, the application provides a method of treating a subject suffering from or susceptible to epilepsy, comprising administering to the subject an effective amount of a compound of the application or a pharmaceutically acceptable salt or solvate thereof. The present application also provides the use of a compound of the application, or a pharmaceutically acceptable salt or solvate thereof, for the preparation of a medicament for administration to a subject suffering from or susceptible to epilepsy for the treatment of epilepsy. The present application also provides a compound of the application, or a pharmaceutically acceptable salt or solvate thereof, for treating a subject suffering from or susceptible to epilepsy.

In one embodiment, the application provides a method for the adjunctive treatment of adults with partial-onset seizures, comprising administering to the subject an effective amount of a compound of the application or a pharmaceutically acceptable salt thereof. The present application also provides the use of a compound of the application, or a pharmaceutically acceptable salt or solvate thereof, for the preparation of a medicament for adjunctive treatment of adults with partial-onset seizures. The present application also provides a compound of the application, or a pharmaceutically acceptable salt or solvate thereof, for adjunctive treatment of adults with partial-onset seizures.

In one embodiment, the present application provides a method of treating or preventing epilepsy, comprising administering a therapeutically effective amount of a compound of the application, or a pharmaceutically acceptable salt or solvate thereof, to a subject in need thereof.

The present application also provides the use of a compound of the application, or a pharmaceutically acceptable salt or solvate thereof, for the preparation of a medicament for administration to a subject for the treatment or prevention of epilepsy. The present application also provides a compound of the application, or a pharmaceutically acceptable salt or solvate thereof, for treating or preventing epilepsy.

In one embodiment, a compound of the application is administered in combination with one or more anti-epileptic drugs (AEDs). There are different types of AEDs. For example, narrow-spectrum AEDs include phenytoin (Dilantin), phenobarbital, carbamazepine (Tegretol), oxcarbazepine (Trileptal), gabapentin (Neurontin), pregabalin (Lyrica), lacosamide (Vimpat), and vigabatrin (Sabril). Broad spectrum AEDs include valproic acid (Depakote), lamotrigine (Lamictal), topiramate (Topamax), zonisamide (Zonegran), levetiracetam (Keppra), clonazepam (Klonopin), and rufinamide (Banzel). In one embodiment, the AED is any AED. In one embodiment, the AED is a narrow spectrum AED. In one embodiment, the AED is a broad spectrum AED.

In one embodiment, the application provides compounds that are useful as analgesics. The compounds are therefore useful in treating or preventing pain. They may be used to improve the condition of a host, typically a human being, suffering from pain. They may be employed to alleviate pain in a host. Thus, the compounds may be used as a preemptive analgesic to treat acute pain such as musculoskeletal pain, post-operative pain and surgical pain, chronic pain such as chronic inflammatory pain (e.g., rheumatoid arthritis and osteoarthritis), neuropathic pain (e.g., post herpetic neuralgia, trigeminal neuralgia and sympathetically maintained pain) and pain associated with cancer and fibromyalgia. The compounds may also be used in the treatment or prevention of pain associated with migraine. The compounds may also be used in the treatment of the pain (both chronic and acute), fever and inflammation of conditions such as rheumatic fever; symptoms associated with influenza or other viral infections, such as the common cold; lower back and neck pain; headache; toothache; sprains and strains; myositis; neuralgia; synovitis; arthritis, including rheumatoid arthritis; degenerative joint diseases, including osteoarthritis; gout and ankylosing spondylitis; tendinitis; bursitis; skin related conditions, such as psoriasis, eczema, burns and dermatitis; injuries, such as sports injuries and those arising from surgical and dental procedures.

In one embodiment, the application provides a method of producing an analgesic effect in a subject in need thereof, comprising administering to the subject an effective amount of a compound of the application or a pharmaceutically acceptable salt or solvate thereof. The present application also provides the use of a compound of the application, or a pharmaceutically acceptable salt or solvate thereof, for the preparation of a medicament for administration to a subject for producing an analgesic effect. The present application also provides a compound of the application, or a pharmaceutically acceptable salt or solvate thereof, for producing an analgesic effect. In one embodiment, the analgesic effect is a neuroprotective effect. In one embodiment, the analgesic effect is a centrally acting analgesic effect.

In one embodiment, the application provides a method of treating or preventing a neurotransmission disorder, CNS disorder, neurodegenerative disease (e.g., Alzheimer's disease, ALS, motor neuron disease, Parkinson's disease, macular degeneration and glaucoma), cognitive disorder, bipolar disorder (e.g., Type I or II bipolar disorder), unipolar depression, or anxiety in a subject in need thereof, comprising administering to the subject an effective amount of a compound of the application or a pharmaceutically acceptable salt or solvate thereof. The present application also provides the use of a compound of the application, or a pharmaceutically acceptable salt or solvate thereof, for the preparation of a medicament for administration to a subject for treating or preventing a neurotransmission disorder, CNS disorder, neurodegenerative disease (e.g., Alzheimer's disease, ALS, motor neuron disease, Parkinson's disease, macular degeneration and glaucoma), cognitive disorder, bipolar disorder (e.g., Type I or II bipolar disorder), unipolar depression, or anxiety. The present application also provides a compound of the application, or a pharmaceutically acceptable salt or solvate thereof, for treating or preventing a neurotransmission disorder, CNS disorder, neurodegenerative disease (e.g., Alzheimer's disease, ALS, motor neuron disease, Parkinson's disease, macular degeneration and glaucoma), cognitive disorder, bipolar disorder (e.g., Type I or II bipolar disorder), unipolar depression, or anxiety.

In one embodiment, the application provides a method of treating or preventing migraine, ataxia, myokimia, tinnitus, and functional bowel disorders (e.g., non-ulcer dyspepsia, non-cardiac chest pain, or irritable bowel syndrome) in a subject in need thereof, comprising administering to the subject an effective amount of a compound of the application or a pharmaceutically acceptable salt or solvate thereof. The present application also provides the use of a compound of the application, or a pharmaceutically acceptable salt or solvate thereof, for the preparation of a medicament for administration to a subject for treating or preventing migraine, ataxia, myokimia, tinnitus, and functional bowel disorders (e.g., non-ulcer dyspepsia, non-cardiac chest pain, or irritable bowel syndrome). The present application also provides a compound of the application, or a pharmaceutically acceptable salt or solvate thereof, for treating or preventing migraine, ataxia, myokimia, tinnitus, and functional bowel disorders (e.g., non-ulcer dyspepsia, non-cardiac chest pain, or irritable bowel syndrome).

In one embodiment, the application provides compounds that are useful in the treatment of CNS disorders such as bipolar disorder, alternatively known as manic depression.

The compounds may thus be used to improve the condition of a human patient suffering from bipolar disorder. They may be used to alleviate the symptoms of bipolar disorder in a host. The compounds may also be used in the treatment of unipolar depression, ataxia, myokimia and anxiety.

In one embodiment, the application provides compounds that are useful in the treatment of neurodegenerative diseases, such as Alzheimer's disease, ALS, motor neuron disease, Parkinson's disease, macular degeneration and glaucoma. The compounds of the application may also be useful in neuroprotection and in the treatment of neurodegeneration following stroke, cardiac arrest, pulmonary bypass, traumatic brain injury, spinal cord injury or the like. In one embodiment, compounds of the application are further useful in the treatment of tinnitus.

In one embodiment, the application provides compounds that are useful in the treatment of functional bowel disorders which include non-ulcer dyspepsia, non-cardiac chest pain and in particular irritable bowel syndrome. Irritable bowel syndrome is a gastrointestinal disorder characterized by the presence of abdominal pain and altered bowel habits without any evidence of organic disease. The compounds may thus be used to alleviate pain associated with irritable bowel syndrome. The condition of a human patient suffering from irritable bowel syndrome may thus be improved.

In one embodiment, the application provides a method of preventing or reducing dependence on, or preventing or reducing tolerance, or reverse tolerance, to a dependence-inducing agent in a subject in need thereof, comprising administering to the subject an effective amount of a compound of the application or a pharmaceutically acceptable salt or solvate thereof. The present application also provides the use of a compound of the application, or a pharmaceutically acceptable salt or solvate thereof, for the preparation of a medicament for administration to a subject for preventing or reducing dependence on, or preventing or reducing tolerance, or reverse tolerance, to a dependence-inducing agent. The present application also provides a compound of the application, or a pharmaceutically acceptable salt or solvate thereof, for preventing or reducing dependence on, or preventing or reducing tolerance, or reverse tolerance, to a dependence-inducing agent. Examples of dependence inducing agents include opioids (e.g., morphine), CNS depressants (e.g., ethanol), psychostimulants (e.g., cocaine) and nicotine.

In one embodiment, the application provides a method of treating or preventing cancer, inflammatory disease, or ophthalmic disease in a subject in need thereof comprising administering to the subject an effective amount of a compound of the application or a pharmaceutically acceptable salt or solvate thereof. The present application also provides the use of a compound of the application, or a pharmaceutically acceptable salt or solvate thereof, for the preparation of a medicament for administration to a subject for treating or preventing cancer, inflammatory disease, or ophthalmic disease. The present application also provides a compound of the application, or a pharmaceutically acceptable salt or solvate thereof, for treating or preventing cancer, inflammatory disease, or ophthalmic disease.

In one embodiment, the application provides compounds that inhibit cellular and neoplastic transformation and metastatic tumor growth and hence are useful in the treatment of certain cancerous diseases, such as colonic cancer.

In one embodiment, the application provides compounds that inhibit inflammatory processes and therefore are of use in the treatment of asthma, allergic rhinitis and respiratory distress syndrome; gastrointestinal conditions such as inflammatory bowel disease, Chron's disease, gastritis, irritable bowel syndrome and ulcerative colitis; and the inflammation in such diseases as vascular disease, migraine, periarteritis nodosa, thyroiditis, aplastic anemia, Hodgkin's disease, sclerodoma, type I diabetes, myasthenia gravis, multiple sclerosis, sorcoidosis, nephrotic syndrome, Bechet's syndrome, polymyositis, gingivitis, conjunctivitis and myocardial ischemia.

In one embodiment, the application provides compounds that are useful in the treatment of ophthalmic diseases such as retinitis, retinopathies, uveitis, and acute injury to the eye tissue.

In one embodiment, the application provides compounds that are useful for the treatment of cognitive disorders such as dementia, particularly degenerative dementia (including senile dementia, Alzheimer's disease, Pick's disease, Huntington's chorea, Parkinson's disease and Creutzfeldt-Jakob disease), and vascular dementia (including multi-infarct dementia), as well as dementia associated with intracranial space occupying lesions, trauma, infections and related conditions (including HIV infection), metabolism, toxins, anoxia and vitamin deficiency; and mild cognitive impairment associated with ageing, particularly Age Associated Memory Loss; and learning deficiencies.

In one embodiment, the application provides a method of producing an anxiolytic effect in a subject in need thereof comprising administering to the subject an effective amount of a compound of the application or a pharmaceutically acceptable salt or solvate thereof. In one embodiment, the application provides a method for the treatment of anxiety and its related psychological and physical symptoms. Anxiolytics have been shown to be useful in the treatment of anxiety disorders. The present application also provides the use of a compound of the application, or a pharmaceutically acceptable salt or solvate thereof, for the preparation of a medicament for administration to a subject for producing an anxiolytic effect. The present application also provides a compound of the application, or a pharmaceutically acceptable salt or solvate thereof, for producing an anxiolytic effect.

In one embodiment, the application provides compounds for treatment. In one embodiment, the application provides compounds for prophylaxis. In one embodiment, the application provides compound for alleviation of established symptoms.

Administration may for example be in the form of tablets, capsules, pills, coated tablets, suppositories, ointments, gels, creams, powders, dusting powders, aerosols or in liquid form. Liquid application forms that may for example be considered are: oils or alcoholic or aqueous solutions as well as suspensions and emulsions. In one embodiment, the application provides forms of application that are tablets that contain between 30 and 60 mg or solutions that contain between 0.1 to 5 percent by weight of active substance.

In one embodiment, a compound of the application is used in human medicine. In one embodiment, the compound of the application is used in veterinary medicine. In one embodiment, a compound of the application is used in agriculture. In one embodiment, a compound of the application is used alone or mixed with other pharmacologically active substances.

The following Examples are illustrative and should not be interpreted in any way so as to limit the scope of the application.

EXAMPLES

Example 1: Synthesis of Compound 1

6-fluoro-2-(2,3,5,6-tetrafluoro-4-nitrophenyl)-1,2,3,4-tetrahydroisoquinoline

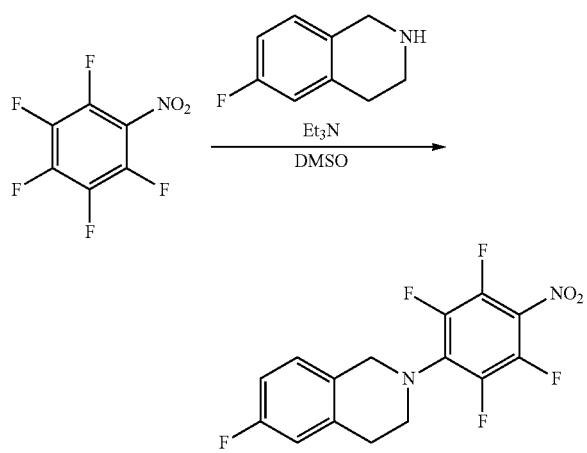

Under air, to 1,2,3,4,5-pentafluoro-6-nitro-benzene (2.13 g, 10.0 mmol, 1.00 equiv) in DMSO (5 mL) at 0° C. were added 6-fluoro-1,2,3,4-tetrahydroisoquinoline (1.51 g, 10.0 mmol, 1.00 equiv) and Et$_3$N (1.67 mL, 12.0 mmol, 1.20 equiv). After stirring for 30 min at 23° C., the reaction mixture was diluted with EtOAc (30 mL), washed with water (3×30 mL) and brine (30 mL), and dried (MgSO$_4$). The filtrate was concentrated in vacuo and the residue was triturated with Et$_2$O to afford 2.40 g of the title compound (70% yield).

NMR Spectroscopy: $^1$H NMR (400 MHz, CDCl$_3$, 23° C., δ): 7.04 (dd, J=7.8, 5.4 Hz, 1H), 6.96-6.87 (m, 2H), 4.59 (s, 2H), 3.67 (t, J=6.0 Hz, 2H), 3.02 (d, J=6.0 Hz, 2H).

2-(2,6-difluoro-3,5-dimethyl-4-nitrophenyl)-6-fluoro-1,2,3,4-tetrahydroisoquinoline

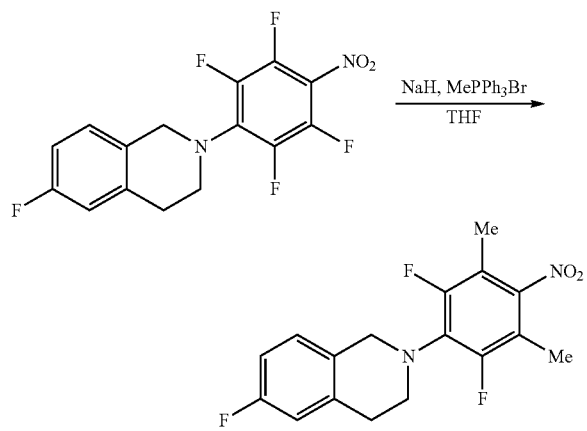

Under nitrogen, to methyltriphenylphosphonium bromide (24.9 g, 69.7 mmol, 10.0 equiv) in THF (350 mL) at 23° C. was added NaH (1.67 g, 69.7 mmol, 10.0 equiv). After stirring for 24 hr at 60° C., the reaction mixture was cooled to 23° C. and 6-fluoro-2-(2,3,5,6-tetrafluoro-4-nitrophenyl)-1,2,3,4-tetrahydroisoquinoline (2.40 g, 6.97 mmol, 1.00 equiv) was added. After stirring for 48 hr at 60° C., the reaction mixture was cooled to 23° C. and water (500 mL) was added dropwise. The phases were separated and the aqueous phase was extracted with EtOAc (2×300 mL). The combined organic phases were washed with brine (300 mL) and dried (MgSO$_4$). The filtrate was concentrated in vacuo and the residue was purified by column chromatography on silica gel eluting with hexanes/EtOAc to afford 1.80 g of the title compound (77% yield).

NMR Spectroscopy: $^1$H NMR (400 MHz, CDCl$_3$, 23° C., δ): 7.01 (dd, J=7.8, 5.4 Hz, 1H), 6.92-6.85 (m, 2H), 4.39 (s, 2H), 3.49 (t, J=6.0 Hz, 2H), 2.90 (d, J=6.0 Hz, 2H), 2.19 (s, 6H).

3,5-difluoro-4-(6-fluoro-3,4-dihydroisoquinolin-2(1H)-yl)-2,6-dimethylaniline

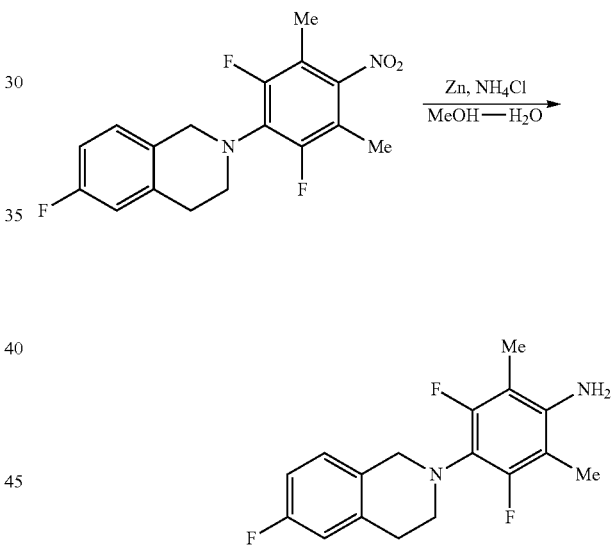

Under air, to 2-(2,6-difluoro-3,5-dimethyl-4-nitrophenyl)-6-fluoro-1,2,3,4-tetrahydroisoquinoline (1.90 g, 5.65 mmol, 1.00 equiv) in MeOH (57 mL) at 23° C. were added Zn powder (1.85 g, 28.3 mmol, 5.00 equiv) and NH$_4$Cl (1.51 g, 28.3 mmol, 5.00 equiv) in H$_2$O (10 mL). After stirring for 1.5 hr at 23° C., the reaction mixture was filtered through a pad of celite. The filtrate was concentrated in vacuo, and H$_2$O (100 mL) and EtOAc (100 mL) were added to the residue. The phases were separated and the aqueous phase was extracted with EtOAc (2×100 mL). The combined organic phases were washed with brine (200 mL) and dried (MgSO$_4$). The filtrate was concentrated in vacuo to afford crude aniline, which was used in the next step without further purification.

N-(3,5-difluoro-4-(6-fluoro-3,4-dihydroisoquinolin-2 (1H)-yl)-2,6-dimethylphenyl)-3,3-dimethylbutanamide (Compound 1)

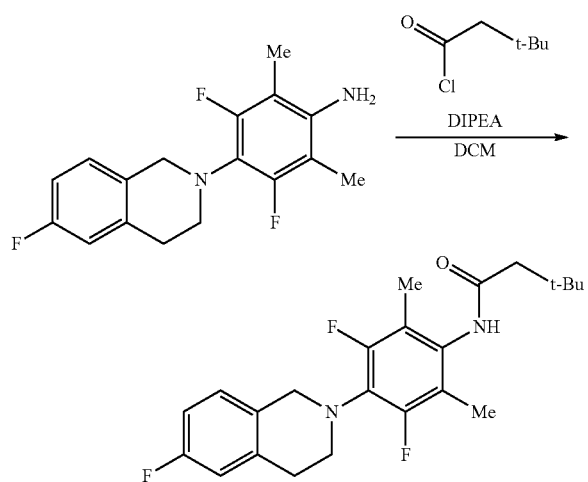

Under nitrogen, to 3,5-difluoro-4-(6-fluoro-3,4-dihydroisoquinolin-2(1H)-yl)-2,6-dimethylaniline obtained above in MeCN (6 mL) at 0° C. were added DIPEA (1.48 mL, 8.48 mmol, 1.50 equiv) and tert-butylacetyl chloride (1.18 mL, 8.48 mmol, 1.50 equiv). After stirring for 1 hr at 23° C., the reaction mixture was concentrated in vacuo, and the residue was purified by column chromatography on silica gel eluting with hexanes/EtOAc to afford 1.00 g of the title compound (44% yield over 2 steps).

NMR Spectroscopy: $^1$H NMR (400 MHz, CDCl$_3$, 23° C., δ): 6.98 (dd, J=7.8, 5.4 Hz, 1H), 6.90-6.80 (m, 2H), 6.64 (s, 1H), 4.30 (s, 2H), 3.43 (t, J=6.0 Hz, 2H), 2.95 (d, J=6.0 Hz, 2H), 2.30 (s, 2H), 2.10 (s, 6H), 1.16 (s, 9H).

Example 2: Synthesis of Compound 2

2,3,5,6-tetrafluoro-N-(4-fluorobenzyl)-4-nitroaniline

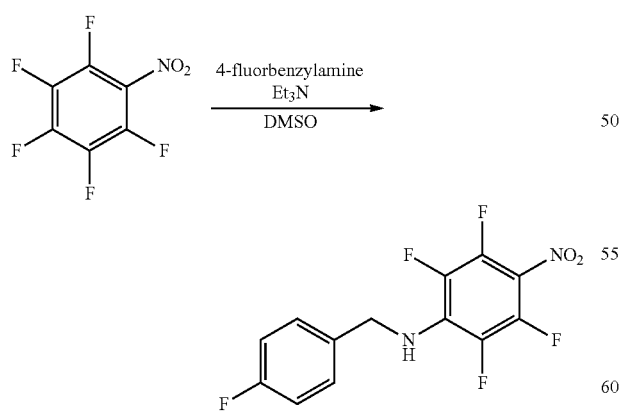

Under air, to 1,2,3,4,5-pentafluoro-6-nitro-benzene (2.13 g, 10.0 mmol, 1.00 equiv) in DMSO (5 mL) at 0° C. were added 4-fluorobenzylamine (1.25 g, 10.0 mmol, 1.00 equiv) and Et$_3$N (1.67 mL, 12.0 mmol, 1.20 equiv). After stirring for 30 min at 23° C., the reaction mixture was diluted with EtOAc (30 mL), washed with water (3×30 mL) and brine (30 mL), and dried (MgSO$_4$). The filtrate was concentrated in vacuo and the residue was purified by chromatography on silica gel eluting with hexanes/EtOAc to afford 1.85 g of the title compound (58% yield).

NMR Spectroscopy: $^1$H NMR (400 MHz, CDCl$_3$, 23° C., δ): 7.30 (dd, J=8.4, 5.4 Hz, 2H), 7.08 (dd, J=8.4, 8.4 Hz, 2H), 4.66 (s, 2H).

tert-butyl 4-fluorobenzyl(2,3,5,6-tetrafluoro-4-nitrophenyl)carbamate

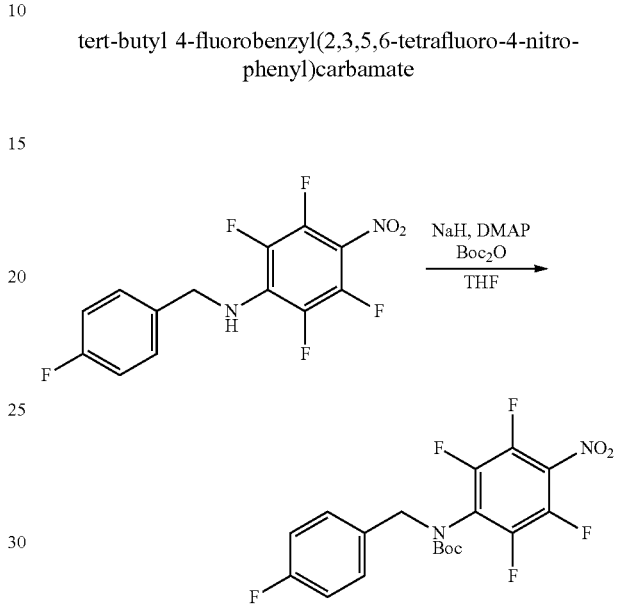

Under nitrogen, to 2,3,5,6-tetrafluoro-N-(4-fluorobenzyl)-4-nitroaniline (1.85 g, 5.81 mmol, 1.00 equiv) in THF (35 mL) at 23° C. were added DMAP (71 mg, 0.58 mmol, 10 mol %), NaH (153 mg, 6.39 mmol, 1.10 equiv), and Boc$_2$O (1.47 mL, 6.39 mmol, 1.10 equiv). After stirring for 1.5 hr at 60° C., the reaction mixture was cooled to 23° C. and water (20 mL) was added dropwise. The phases were separated and the aqueous phase was extracted with EtOAc (2×20 mL). The combined organic phases were washed with brine (20 mL) and dried (MgSO$_4$). The filtrate was concentrated in vacuo and the residue was purified by column chromatography on silica gel eluting with hexanes/EtOAc to afford 1.50 g of the title compound (62% yield).

NMR Spectroscopy: $^1$H NMR (400 MHz, CDCl$_3$, 23° C., δ): 7.20 (dd, J=8.4, 5.4 Hz, 2H), 6.98 (dd, J=8.4, 8.4 Hz, 2H), 4.81 (s, 2H), 1.44 (br s, 9H).

tert-butyl (2,6-difluoro-3,5-dimethyl-4-nitrophenyl)(4-fluorobenzyl)carbamate

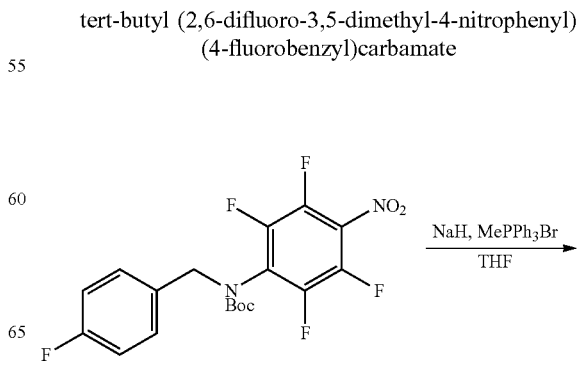

-continued

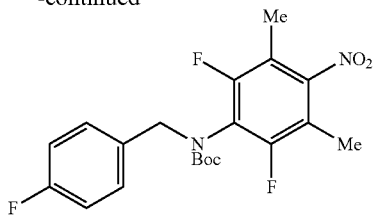

Under nitrogen, to methyltriphenylphosphonium bromide (12.8 g, 35.9 mmol, 10.0 equiv) in THF (250 mL) at 23° C. was added NaH (862 mg, 35.9 mmol, 10.0 equiv). After stirring for 24 hr at 60° C., the reaction mixture was cooled to 23° C. and tert-butyl 4-fluorobenzyl(2,3,5,6-tetrafluoro-4-nitrophenyl)carbamate (1.50 g, 3.59 mmol, 1.00 equiv) was added. After stirring for 48 hr at 60° C., the reaction mixture was cooled to 23° C. and water (300 mL) was added dropwise. The phases were separated and the aqueous phase was extracted with EtOAc (2×200 mL). The combined organic phases were washed with brine (300 mL) and dried (MgSO$_4$). The filtrate was concentrated in vacuo and the residue was purified by column chromatography on silica gel eluting with hexanes/EtOAc to afford 1.06 g of the title compound (72% yield).

NMR Spectroscopy: $^1$H NMR (400 MHz, CDCl$_3$, 23° C., δ): 7.22-7.18 (m, 2H), 7.02-6.89 (m, 2H), 4.73 (s, 2H, major isomer), 4.67 (s, 2H, minor isomer), 2.14 (br s, 6H), 1.50 (s, 9H, minor isomer), 1.39 (s, 9H, major isomer). *A mixture of rotational isomers was observed in the NMR time scale, which complicated the further structural analysis.

tert-butyl (4-amino-2,6-difluoro-3,5-dimethylphenyl) (4-fluorobenzyl)carbamate

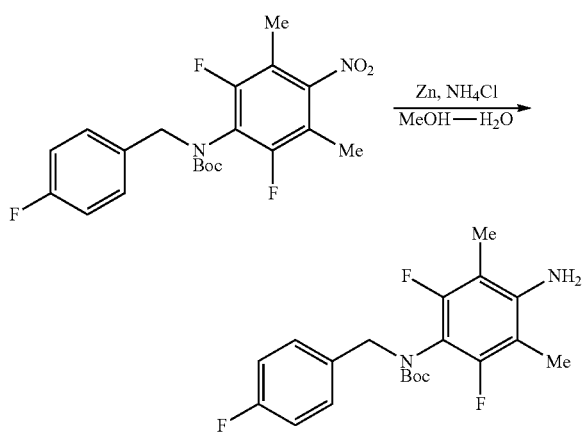

Under air, to 2-(2,6-difluoro-3,5-dimethyl-4-nitrophenyl)-6-fluoro-1,2,3,4-tetrahydroisoquinoline (1.06 g, 2.58 mmol, 1.00 equiv) in MeOH (26 mL) at 23° C. were added Zn powder (844 mg, 12.9 mmol, 5.00 equiv) and NH$_4$Cl (690 mg, 12.9 mmol, 5.00 equiv) in H$_2$O (5 mL). After stirring for 1.5 hr at 23° C., the reaction mixture was filtered through a pad of celite. The filtrate was concentrated in vacuo, and H$_2$O (100 mL) and EtOAc (100 mL) were added to the residue. The phases were separated and the aqueous phase was extracted with EtOAc (2×100 mL). The combined organic phases were washed with brine (200 mL) and dried (MgSO$_4$). The filtrate was concentrated in vacuo to afford crude aniline, which was used in the next step without further purification.

tert-butyl (4-(3,3-dimethylbutanamido)-2,6-difluoro-3,5-dimethylphenyl) (4-fluorobenzyl)carbamate

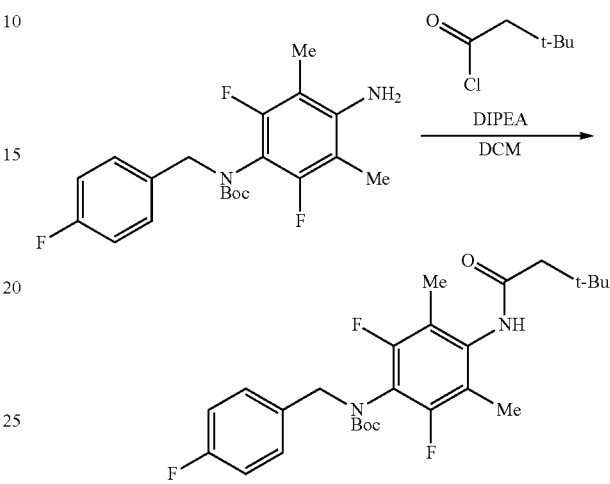

Under nitrogen, to tert-butyl (4-amino-2,6-difluoro-3,5-dimethylphenyl)(4-fluorobenzyl)carbamate obtained above in MeCN (4 mL) at 0° C. were added DIPEA (0.674 mL, 3.87 mmol, 1.50 equiv) and tert-butylacetyl chloride (0.538 mL, 3.87 mmol, 1.50 equiv). After stirring for 1 hr at 23° C., the reaction mixture was concentrated in vacuo to afford crude acylation product, which was used in the next step without further purification.

N-(3,5-difluoro-4-((4-fluorobenzyl)amino)-2,6-dimethylphenyl)-3,3-dimethylbutanamide (Compound 2)

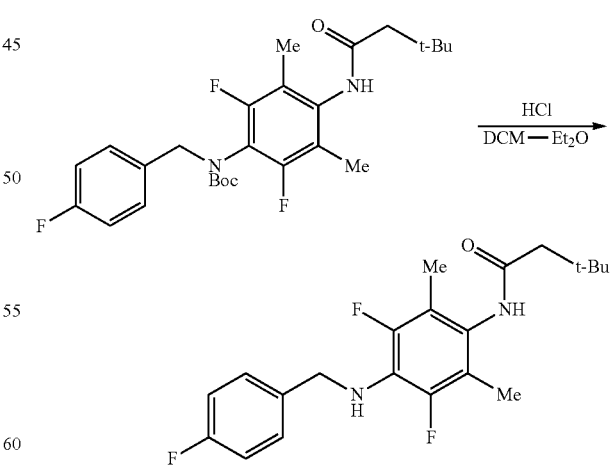

Under nitrogen, to tert-butyl (4-(3,3-dimethylbutanamido)-2,6-difluoro-3,5-dimethylphenyl)(4-fluorobenzyl) carbamate obtained above in DCM (13 mL) at 23° C. was added HCl (2.0 M in Et$_2$O, 12.9 mL, 25.8 mmol, 10.0 equiv). After stirring for 3 hr at 23° C., NaHCO$_3$ (aq) (20 mL) was added to the reaction mixture. The phases were separated and the aqueous phase was extracted with EtOAc (2×20 mL). The combined organic phases were washed with brine (20 mL) and dried (MgSO$_4$). The filtrate was concentrated in vacuo and the residue was purified by column chromatography on silica gel eluting with hexanes/EtOAc to afford 670 mg of the title compound (69% yield over 3 steps).

NMR Spectroscopy: $^1$H NMR (300 MHz, methanol-d4, 23° C., δ): 7.31 (dd, J=8.4, 5.4 Hz, 2H), 6.98 (dd, J=8.4, 8.4 Hz, 2H), 4.40 (s, 2H), 2.27 (s, 2H), 2.02 (br s, 6H), 1.10 (s, 9H).

Example 3: Synthesis of Compound 3

Compound 3 is synthesized in a similar way as Compound 1 using the corresponding commercially available 4-methoxypiperidine in place of 6-fluoro-1,2,3,4-tetrahydroisoquinoline.

Example 4: Synthesis of Compound 4

Compound 4 is synthesized in a similar way as Compound 1 using the corresponding commercially available ethyltriphenylphosphonium bromide in place of methyltriphenylphosphonium bromide.

Example 5: Synthesis of Compound 5

Compound 5 is synthesized in a similar way as Compound 2 using the corresponding commercially available ethyltriphenylphosphonium bromide in place of methyltriphenylphosphonium bromide.

Example 6: Synthesis of Compound 6

Compound 6 is synthesized in a similar way as Compound 3 using the corresponding commercially available ethyltriphenylphosphonium bromide in place of methyltriphenylphosphonium bromide.

Example 7: Assessment of Recombinantly Expressed Human Kv7.2/7.3 Channels Activation Ability The in vitro effects of a compound of the present application recombinantly expressed human Kv7.2/7.3 channels are assessed on Syncropatch high throughput electrophysiology platform.

Cell Preparations:

CHO cells stably expressing human Kv7.2/7.3 channels were cultured in Ham's F-12 media (Hyclone, Cat # SH30022.02) supplemented with 10% Fetal Bovine Serum, 1×MEM non-essential amino acids, and 400 μg/ml G418 at 37° C. in 5% CO$_2$. On the day of Syncropatch, the cells were washed once in DPBS (Hyclone, Cat # SH30028.03) for approximately 30 seconds. 1 ml of 1×0.015% Trypsin-EDTA GIBCO Cat #25300-054) was added and swirled around to cover the bottom of the flask, and allowed to sit on the cells for about 4 minutes (approximately 90% of the cells were lifted by light tapping of the flask). 10 ml of cold media (Ham's F-12 media (Hyclone, Cat # SH30022.02) supplemented with 10% Fetal Bovine Serum, 1×MEM non-essential amino acids, and 400 μg/ml G418) was added to inactivate Trypsin. The cells were then triturated until a single cell suspension was achieved, and the cell count was performed. The cells were then diluted to a concentration of 5×10$^5$/ml and placed into the "cell hotel" on the deck of the Syncropatch at 10° C. for about 1 hour to recover. 40 μL of the cell suspension was dispensed into each well of a 384-well Syncropatch chip by the onboard pipettor at the beginning of each Syncropatch assay.

Test Solution Preparations.

The compounds to be tested were dissolved in DMSO to give 10 mM stock solutions. Eight-point dose response curves were created by performing semi-log serial dilutions from 10 mM compound stock solutions in 100% DMSO. Concentration-response curves were transferred to assay plates to give two-fold final compound concentration to account for the two-fold dilution with drug addition on the SyncroPatch. Final DMSO concentration in the assay was 0.3%. Final assay test concentrations were 30 μM to 0.01 μM or 1 μM to 0.0003 μM. Negative (0.3% DMSO) and positive (30 μM ML213) controls were included in each test run to assess pharmacological responsiveness.

Assessment Protocol:

Electrophysiological studies of the compounds were performed using the Nanion SyncroPatch automated patch clamp platform. Compound effects on Kv7 channels were assayed using a voltage protocol as shown in FIG. 1.

Kv7 channels were evaluated using a voltage protocol in which cells were voltage-clamped at a holding potential of −110 mV. Potassium currents were activated with a series of voltage steps from −110 mV to +50 mV in 10 mV intervals with 5.5 seconds between successive voltage steps. Each voltage step was 3 seconds in duration and immediately followed by a 1 second voltage step to −120 mV to generate an inward "tail" current to allow construction of activation (G-V) curves by plotting normalized peak tail current versus the potential of the activating voltage step. To obtain normalized values, peak current amplitudes for successive depolarizing pulses were normalized against the maximum tail current amplitude generated at +50 mV (Tatulian et al., *Journal of Neuroscience* 2001, 21 (15)).

Data Analysis:

Data was collected on the Syncropatch platform using PatchControl software (Nanion) and processed and analyzed using DataControl Software (Nanion). Normalized percent activation was calculated and activation curves were fit with a Boltzmann function to determine the midpoint voltage of activation (G-V midpoint) for both pre-compound and post-compound conditions for each of the 384-wells of a sealchip with Pipeline Pilot (Accelrys). The difference in G-V midpoint between pre-compound and post-compound conditions (Δ V0.5) was plotted as a function of concentration and concentration-response curves were fit with a three-parameter logistic equation {Y=Bottom+(Top−Bottom)/(1+10^(Log EC50−X))} for determination of the EC$_{50}$ (Graphpad Prism).

Assessment Results:

Exemplary compounds of the present application were tested for their ability to produce a concentration-dependent hyperpolarizing shift in the midpoint of activation for heteromeric Kv7.2/7.3 channels. Eight of the compounds produced a quantifiable hyperpolarizing shift in activation as determined by a concentration-dependent shift in the midpoint that could be fit with a 3-parameter logistic equation. These data were combined with the initial 8-point concentration-response data in a single fit. Potency and efficacy data for each compound are summarized in Table 2.

TABLE 2

| Compound No. | KCNQ2/3 EC$_{50}$ | KCNQ3/5 EC$_{50}$ | KCNQ4 EC$_{50}$ | Selectivity KCNQ3/5 EC50 KCNQ2/3 EC50 | KCNQ4 EC50 KCNQ2/3 EC50 |
|---|---|---|---|---|---|
| Control | A | A | B | I | IV |
| 1 | B | C | D | III | VI |
| 2 | A | B | C | IV | V |

A: <0.1 µM,
B: 0.1 to <1 µM,
C: 1 to <10 µM,
D: ≥10 µM.
I: <1,
II: 1 to <5,
III: 5 to <10,
IV: 10 to <50,
V: 50 to <100,
VI: ≥100.

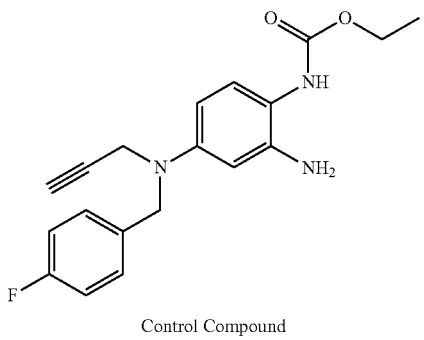 [SMILES: C#CCN(Cc1ccc(F)cc1)c1ccc(NC(=O)OCC)c(N)c1]

Control Compound

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound of formula A:

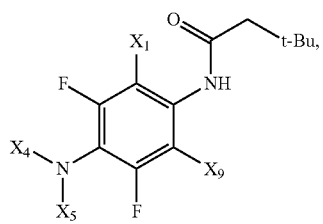

(A)

or a pharmaceutically acceptable salt or solvate thereof, wherein:

$X_1$ and $X_9$ are each independently methyl or ethyl;
$X_4$ is H, $C_1$-$C_4$ alkyl, $C_2$-$C_6$ alkenyl, or $C_2$-$C_6$ alkynyl;
$X_5$ is phenyl-$(CX_8X_8)_m$, wherein the phenyl is optionally substituted with one or more substituents independently selected from deuterium, F, SF$_5$, $C_1$-$C_4$ alkyl, $C_1$-$C_4$ alkyl substituted with one or more F, $C_1$-$C_4$ alkoxy, and $C_1$-$C_4$ alkoxy substituted with one or more F; or $X_4$ and $X_5$, together with the nitrogen atom to which they are attached, form a 5- to 7-membered heterocyclic ring comprising 1 or 2 heteroatoms selected from N, O, and S, wherein the heterocyclic ring is optionally substituted with one or more substituents independently selected from deuterium, F, SF$_5$, $C_1$-$C_4$ alkyl, $C_1$-$C_4$ alkyl substituted with one or more F, $C_1$-$C_4$ alkoxy, and $C_1$-$C_4$ alkoxy substituted with one or more F, or two substituents attached to adjacent carbon atoms on the heterocyclic ring, together with the carbon atoms to which they are attached, form a phenyl optionally substituted with one or more substituents independently selected from deuterium, F, SF$_5$, $C_1$-$C_4$ alkyl, $C_1$-$C_4$ alkyl substituted with one or more F, $C_1$-$C_4$ alkoxy, and $C_1$-$C_4$ alkoxy substituted with one or more F;

each $X_8$ is independently H, deuterium, F, $C_1$-$C_4$ alkyl, or $C_1$-$C_4$ alkyl substituted with one or more F; and
m is 1, 2, or 3.

2. The compound of claim 1, being of formula Ia or Ib:

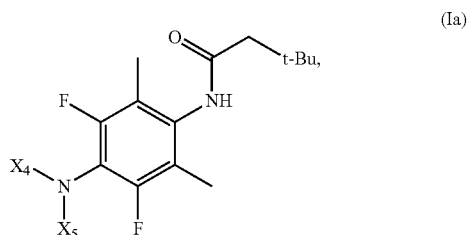

(Ia)

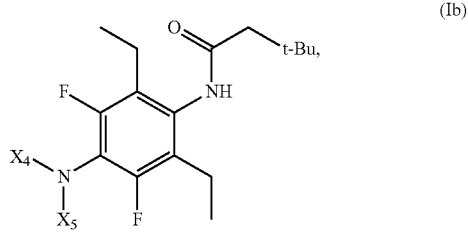

(Ib)

or a pharmaceutically acceptable salt or solvate thereof.

3. The compound of claim 1, wherein $X_4$ is H.

4. The compound of claim 1, wherein $X_4$ is $C_1$-$C_4$ alkyl, $C_2$-$C_6$ alkenyl, or $C_2$-$C_6$ alkynyl.

5. The compound of claim 1, wherein $X_5$ is phenyl-$(CX_8X_8)$, phenyl-$(CX_8X_8)_2$, or phenyl-$(CX_8X_8)_3$, wherein the phenyl is optionally substituted with one or more substituents independently selected from deuterium, F, SF$_5$, $C_1$-$C_4$ alkyl, $C_1$-$C_4$ alkyl substituted with one or more F, $C_1$-$C_4$ alkoxy, and $C_1$-$C_4$ alkoxy substituted with one or more F.

6. The compound of claim 5, wherein $X_5$ is phenyl-$(CX_8X_8)$.

7. The compound of claim 5, wherein the phenyl is substituted with one or more substituents independently selected from F, CF$_3$, and OCF$_3$.

8. The compound of claim 1, wherein $X_4$ and $X_5$, together with the nitrogen atom to which they are attached, form a 5- to 7-membered heterocyclic ring comprising 1 or 2 heteroatoms selected from N, O, and S, wherein the heterocyclic ring is optionally substituted with one or more substituents independently selected from deuterium, F, SF$_5$, $C_1$-$C_4$ alkyl, $C_1$-$C_4$ alkyl substituted with one or more F, $C_1$-$C_4$ alkoxy, and $C_1$-$C_4$ alkoxy substituted with one or more F.

9. The compound of claim 8, wherein the heterocyclic ring is substituted with one or more substituents independently selected from $CH_3$ and $OCH_3$.

10. The compound of claim 8, wherein the heterocyclic ring is pyrrolidinyl, tetrahydrofuranyl, tetrahydrothiophenyl, oxazolidinyl, isoxazolidinyl, thiazolidinyl, isothiazolidinyl, piperidinyl, piperazinyl, tetrahydropyranyl, tetrahydrothiapyranyl, dioxanyl, morpholinyl, oxazinanyl, thiazinanyl, or oxathianyl.

11. The compound of claim 1, wherein $X_4$ and $X_5$, together with the nitrogen atom to which they are attached, form a 5- to 7-membered heterocyclic ring substituted with two or more substituents, wherein two substituents attached to adjacent carbon atoms on the heterocyclic ring, together with the carbon atoms to which they are attached, form a phenyl optionally substituted with one or more substituents independently selected from deuterium, F, $SF_5$, $C_1$-$C_4$ alkyl, $C_1$-$C_4$ alkyl substituted with one or more F, $C_1$-$C_4$ alkoxy, and $C_1$-$C_4$ alkoxy substituted with one or more F.

12. The compound of claim 11, wherein $X_4$ and $X_5$, together with the nitrogen atom to which they are attached, form a heterocyclic ring selected from

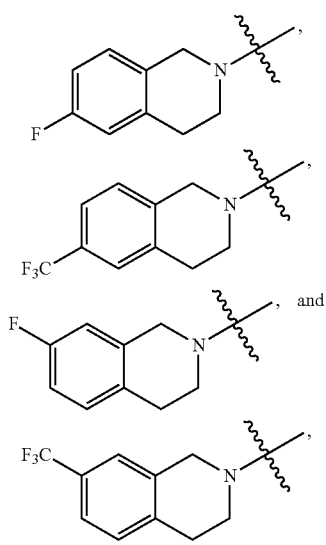

wherein the nitrogen atom is the nitrogen atom bonded to $X_4$ and $X_5$.

13. The compound of claim 1, being of formula IIa or IIb:

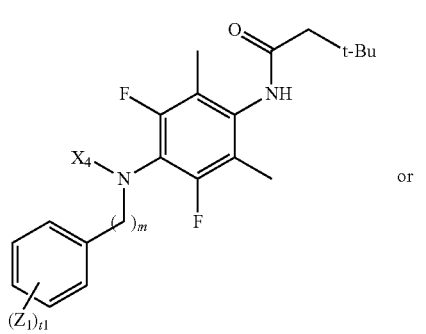

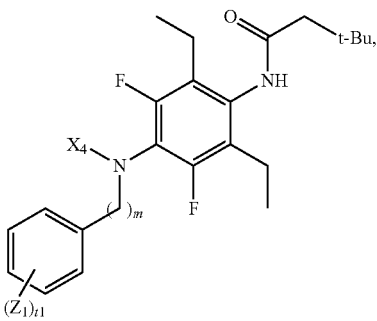

or a pharmaceutically acceptable salt or solvate thereof, wherein:

$X_4$ is H, $C_1$-$C_4$ alkyl, $C_2$-$C_6$ alkenyl, or $C_2$-$C_6$ alkynyl;

t1 is 1, 2, 3, 4, or 5;

each $Z_1$ is independently selected from deuterium, F, $SF_5$, $C_1$-$C_4$ alkyl, $C_1$-$C_4$ alkyl substituted with one or more F, $C_1$-$C_4$ alkoxy, and $C_1$-$C_4$ alkoxy substituted with one or more F; and m is 1, 2, or 3.

14. The compound of claim 1, being of formula IIIa or IIIb:

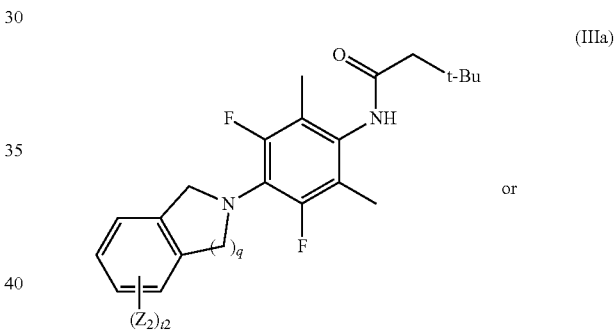

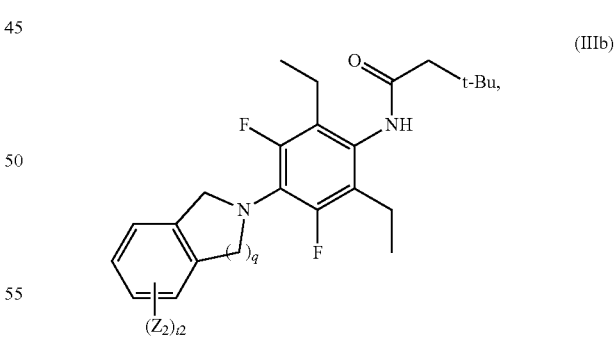

or a pharmaceutically acceptable salt or solvate thereof, wherein:

q is 1, 2, or 3;

t2 is 1, 2, 3, or 4; and each $Z_2$ is independently selected from deuterium, F, $SF_5$, $C_1$-$C_4$ alkyl, $C_1$-$C_4$ alkyl substituted with one or more F, $C_1$-$C_4$ alkoxy, and $C_1$-$C_4$ alkoxy substituted with one or more F.

15. The compound of claim 1, being of formula IVa or IVb:

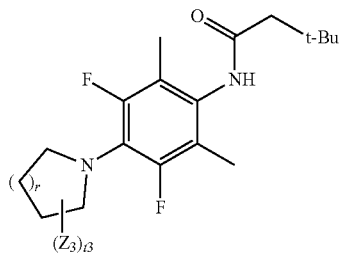
(IVa)

or

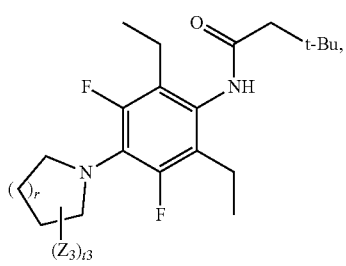
(IVb)

or a pharmaceutically acceptable salt or solvate thereof, wherein:

r is 1, 2, or 3;
t3 is 1, 2, 3, or 4; and
each $Z_3$ is independently selected from deuterium, F, $SF_5$, $C_1$-$C_4$ alkyl, $C_1$-$C_4$ alkyl substituted with one or more F, $C_1$-$C_4$ alkoxy, and $C_1$-$C_4$ alkoxy substituted with one or more F.

16. The compound of claim 1, being selected from the groups consisting of

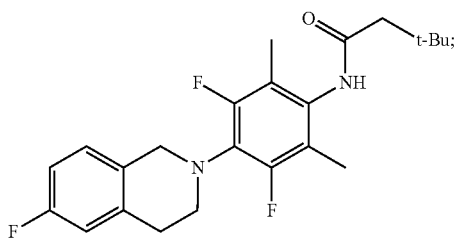

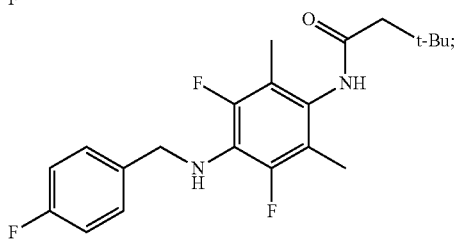

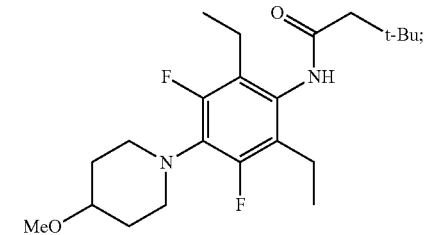

-continued and pharmaceutically acceptable salts and solvates thereof.

17. A pharmaceutical composition comprising at least one compound of claim 1 or a pharmaceutically acceptable salt or solvate thereof and one or more pharmaceutically acceptable carrier or excipient.

* * * * *

UNITED STATES PATENT AND TRADEMARK OFFICE
CERTIFICATE OF CORRECTION

PATENT NO. : 10,676,437 B2
APPLICATION NO. : 16/218759
DATED : June 9, 2020
INVENTOR(S) : Takeru Furuya et al.

Page 1 of 1

It is certified that error appears in the above-identified patent and that said Letters Patent is hereby corrected as shown below:

In the Specification

At Column 8, Line number 11, replace:
"each $X_5$ is independently H, deuterium, F, $C_1$-$C_4$ alkyl, or"
With:
--each $X_8$ is independently H, deuterium, F, $C_1$-$C_4$ alkyl, or--

In the Claims

At Column 54, Claim number 1, Line number 18, replace:
"each $X_5$ is independently H, deuterium, F, $C_1$-$C_4$ alkyl, or"
With:
--each $X_8$ is independently H, deuterium, F, $C_1$-$C_4$ alkyl, or--

Signed and Sealed this
Twenty-eighth Day of July, 2020

Andrei Iancu
*Director of the United States Patent and Trademark Office*